United States Patent [19]
Muenster et al.

[11] Patent Number: 5,276,009
[45] Date of Patent: Jan. 4, 1994

[54] DICARBOXIMIDES AND THEIR USE AS HERBICIDES

[75] Inventors: Peter Muenster, Neulussheim; Wolfgang Freund, Neustadt; Gerd Steiner, Kirchheim; Helmut Walter, Obrigheim; Karl-Otto Westphalen, Speyer; Matthias Gerber, Mutterstadt, all of Fed. Rep. of Germany

[73] Assignee: BASF Aktiengesellschaft, Ludwigshafen, Fed. Rep. of Germany

[21] Appl. No.: 732,794

[22] Filed: Jul. 19, 1991

[30] Foreign Application Priority Data

Jul. 20, 1990 [DE] Fed. Rep. of Germany ....... 4023048

[51] Int. Cl.$^5$ ................. C07D 491/04; C07D 495/04; A01N 43/72
[52] U.S. Cl. ..................... 504/284; 548/453
[58] Field of Search ................. 548/453; 504/284

[56] References Cited

FOREIGN PATENT DOCUMENTS 0259264  3/1988  European Pat. Off. .
2509922  9/1975  Fed. Rep. of Germany .
2538951  3/1977  Fed. Rep. of Germany .
3402026  7/1985  Fed. Rep. of Germany .
3901074  7/1990  Fed. Rep. of Germany .

OTHER PUBLICATIONS

The Journal of Chemical Society, 1937, pp. 911–921, R. P. Linstead, et al., "Phthalocyanines. Part IX. Derivatives of Thiophen, Thionaphthen, Pyridine and Pyrazine, and a Note on the Nomenclature".
Journal of Synthetic Organic Chemistry, 1988, No. 7, Jul. 1988, pp. 499–500, D. P. Curran, "Synthesis".
Berichte der Deutschen Chemischen Gesellschaft, 1925, vol. 2, No. 58, pp. 1782–1787, R. Seka, "Zur Kenntnis Heterocyclischer Ringsysteme".
The Journal of Chemical Society, Chemical Communications, 1984, No. 13, I. G. Pitt, et al., "The Generation and Trapping of a Novel Dewar Furan", pp. 1466–1467.
Chemische Berichte, vol. 111, No. 7, 1978, pp. 3029–3036, H. Gotthardt, et al., "[3+2]-Cycloadditionen Mesoionischer 1, 3-Dithiolone an Ethylendicarbonsaure-Derivate und 1, 2-Dibenzoylethylen$^1$)".
The Journal of Organic Chemistry, vol. 19, 1954, pp. 70–73, J. Sice, "Substituted Thenoic Acids".
Egypt. J. Chem., vol. 24, No. 5, 1981, pp. 371–373, M. El Borai, "The Reaction of Isocyanate with Diformyl-Thiophene".

Primary Examiner—David B. Springer
Attorney, Agent, or Firm—Oblon, Spivak, McClelland, Maier & Neustadt

[57] ABSTRACT

Dicarboximides of the general formulae Ia and Ib where
X is oxygen or sulfur, $R^1$ is hydrogen, cycloalkyl, alkyl, hydroxyl, alkoxy, cyanoalkyl, alkenyl, alkynyl, phenyl, naphthyl or a 5-membered or 6-membered heterocyclic structure, where the stated radicals may be substituted, and
$R^2$ and $R^3$ are each nitro, cyano, halogen, amino, mono- or dialkylamino, alkylcarbonylamino, unsubstituted or halogen-substituted alkoxy or alkylthio, alkylsulfonyl, haloalkylsulfonyl, alkenyl, alkynyl, phenyl, phenoxy or phenylthio or one of the radicals $R^1$, with the proviso that specific compounds named in the description are excluded.

Processes for the preparation of the compounds Ia and Ib and herbicides containing them.

8 Claims, No Drawings

DICARBOXIMIDES AND THEIR USE AS HERBICIDES

The present invention relates to dicarboximides of the general formulae Ia and Ib

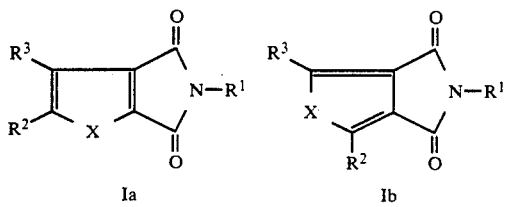

where
X is oxygen or sulfur;
R$^1$ is hydrogen or hydroxyl;
C$_3$-C$_8$-cycloalkyl which may carry from one to three of the following radicals: halogen, C$_1$-C$_4$-alkyl, C$_1$-C$_4$-haloalkyl,
C$_1$-C$_4$-alkoxy and/or C$_1$-C$_4$-haloalkoxy;
C$_1$-C$_6$-alkyl which may carry from one to three of the following radicals: hydroxyl, halogen, cyano, C$_3$-C$_8$-cycloalkyl, C$_1$-C$_4$-alkoxy, C$_1$-C$_4$-haloalkoxy, C$_1$-C$_4$-alkylthio,
C$_1$-C$_4$-haloalkylthio, C$_1$-C$_4$-alkylamino, di-C$_1$-C$_4$-alkylamino and/or C$_3$-C$_6$-Cycloalkylamino and/or a radical

in which
R is cyano, nitro, halogen, C$_1$-C$_4$-alkyl, C$_1$-C$_4$-haloalkyl,
C$_1$-C$_4$-alkoxy, C$_1$-C$_4$-haloalkoxy, C$_2$-C$_4$-alkynyloxy C$_1$-C$_4$-alkylthio, C$_1$-C$_4$-haloalkylthio, C$_3$-C$_6$-alkoxycarbonylalkoxy,
C$_1$-C$_4$-alkoxycarbonyl, 2-alkoxycarbonyl-prop-1-enyl, C$_1$-C$_4$-alkanoyl, C$_1$-C$_4$-haloalkanoyl, formyl, 2-dioxolanyl and/or phenyl and
m is 0, 1, 2 or 3, and the radicals R may be different when m is 2 or 3;
C$_1$-C$_4$-alkoxy, C$_2$-C$_6$-cyanoalkyl, C$_3$-C$_6$-alkenyl, C$_3$-C$_6$-alkynyl, phenyl or naphthyl, where these groups may carry from one to three of the radicals stated for R;
a 5-membered or 6-membered saturated or unsaturated heterocyclic structure containing one or two hetero atoms selected from the group consisting of nitrogen, oxygen or sulfur, where this ring may carry one or two of the following radicals: halogen, C$_1$-C$_4$-alkyl, C$_1$-C$_4$-haloalkyl, C$_1$-C$_4$-alkoxyl C$_1$-C$_4$-haloalkoxy and/or C$_1$-C$_4$-alkylthio, or di-C$_1$-C$_4$-alkylamino;
R$^2$ and R$^3$ are each nitro, cyano, halogen;
amino which may carry one or two C$_1$-C$_4$-alkyl groups and/or a C$_1$-C$_4$-alkylcarbonyl group;
C$_1$-C$_4$-alkoxy or C$_1$-C$_4$-alkylthio, where these groups may carry from one to nine halogen atoms;
C$_1$-C$_4$-alkylsulfonyl, C$_1$-C$_4$-haloalkylsulfonyl;
C$_2$-C$_6$-alkenyl, C$_2$-C$_6$-alkynyl, phenyl, phenoxy or phenylthio, where these groups may carry from one to three of the radicals stated for R, or
one of the groups stated for R$^1$,
with the proviso that, in the case of the dicarboximide Ia where X is sulfur,
R$^1$ is not hydrogen or 2-methyl-4-nitrophenyl when R$^2$ and R$^3$ are each hydrogen,
and furthermore with the proviso that, in the case of the dicarboximide Ib where X is oxygen,
R$^1$ is not phenyl or hydrogen when R$^2$ and R$^3$ are each phenyl and
all radicals R$^1$-R$^3$ are not simultaneously methyl,
and finally with the proviso that, in the case of the dicarboximides Ib where X is sulfur,
R$^1$ is not phenyl, 2-phenylethyl, ethyl, hexyl, 2-hydroxyethyl, 2-hydroxypropyl or ethoxycarbonylmethyl when R$^2$ and R$^3$ are each phenyl,
R$^1$ is not 3-methoxypropyl when R$^2$ and R$^3$ are each 4-chlorophenyl,
R$^1$ is not phenyl when R$^2$ and R$^3$ are each hydrogen and
all radicals R$^1$-R$^1$ are not simultaneously hydrogen,
and agriculturally useable salts of the compounds Ia or Ib.

The present invention furthermore relates to a process for the preparation of the compounds Ia and Ib and herbicides containing at least one dicarboximide Ia or Ib and/or one dicarboximide of the general formulae IA and IB

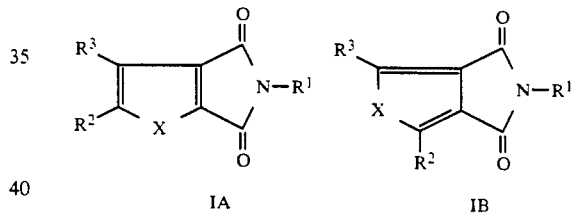

in which the substituents have the meanings stated in claim 1 and in addition the compounds excluded there may be present.

Dicarboximides of the formula Ia where X is sulfur are disclosed in DE-A 25 09 922, J. Chem. Soc. 1937, page 911 and DE-A 34 02 026 or Synthesis 1988, 499 et seq. Dicarboximides of the formula Ib where X is oxygen are disclosed in Chem. Ber. 58 (1925), 1783-1787 and Chem. Commun. 22 (1984), 1466-67. Dicarboximides of the formula Ib where X is sulfur are disclosed in Chem. Ber. 111 (1978), 3029-3036, DE-A 25 38 951, J. Org. Chem. 19 (1954), 70 and Egypt. J. Chem. 24 (1981), 371-373. The cited prior art gives no indication of herbicidal properties of the dicarboximides.

It is an object of the present invention to provide novel herbicidal substances.

We have found that this object is achieved by the type of carboximides Ia and Ib defined at the outset and processes for their preparation. We have furthermore found that both the dicarboximides Ia and Ib and the dicarboximides IA and IB are suitable for controlling undesirable plant growth.

The novel dicarboximides Ia and Ib can be prepared by various methods. They are obtained, for example, by the following processes.

Method A

By removal of water using water-eliminating agents, for example acetic anhydride or inorganic acyl halides, the compounds II and III are converted into the dicarboximides of the formula Ia. The reaction is advantageously advantageously carried out by a procedure in which the carboxamides in an inert organic solvent are initially taken and a roughly molar amount of a water-eliminating agent, if necessary likewise in solution in an inert solvent, is added dropwise. The mixture can be worked up in a conventional manner, for example by hydrolysis with water and filtration under suction or extraction of the product with an organic solvent and evaporation of the organic solvent:

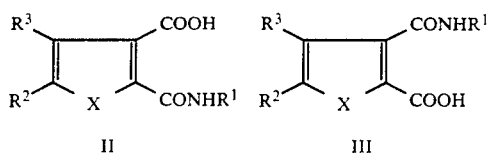

The reaction can be carried out at from $-10°$ C. to the reflux temperature of the particular solvent, preferably at from $0°$ to $150°$ C.

The molar ratios in which the required starting compounds are reacted with one another are in general from 0.9:1 to 5:1 for the ratio of water-eliminating agent to amide.

The concentration of the educts in the solvent (mixture) is in general from 0.1 to 5, preferably from 0.2 to 2, mol/l.

The dicarboxylic acid monoamides II to V which are used as starting materials can be synthesized by various methods.

The dicarboxylic acid monoamides II–V can be obtained, for example, by converting the corresponding carboxylic acid of the formula IX a–d in a conventional manner to the halide or into another activated form of the carboxylic acid, then reacting this derivative with an amine of the formula VIII and thereafter reacting the resulting amide X a–d with a carboxylating reagent in the presence of a base.

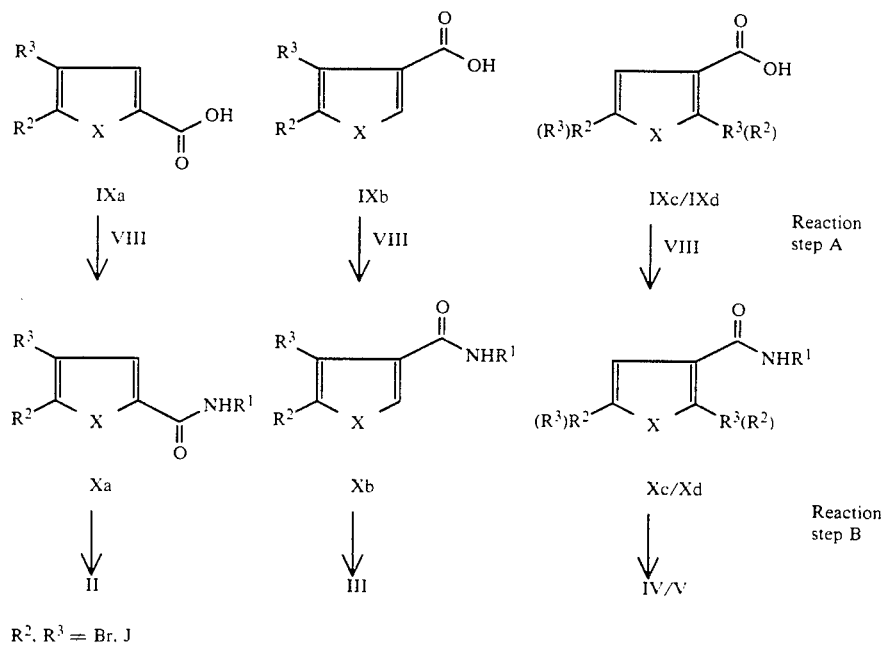

Solvents such as halohydrocarbons, e.g. tetrachloroethane, methylene chloride, chloroform, dichloroethane, chlorobenzene or 1,2-dichlorobenzene, ethers, eg. diethyl ether, methyl tert-butyl ether, dimethoxyethane, diethylene glycol diethyl ether, tetrahydrofuran or dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone or 1,3-dimethylimidazolin-2-one, aromatics, e.g. benzene, toluene, xylene, pyridine or quinoline, ketones, e.g. acetone or methyl ethyl ketone, or corresponding mixtures are advantageously used for these reactions.

Water-eliminating agents are, for example, anhydrides of lower alkanoic acids, such as acetic anhydride, propanephosphonic anhydride, toluenesulfonyl chloride/pyridine, thionyl chloride or phosphorus tri- or pentabromide or -chloride.

The individual reaction steps of this synthesis sequence can be carried out in general as follows:

Reaction step A

The compounds Xa–d are obtained from the acids IXa–d by converting IXa–d in a conventional manner into the halide or into another activated form of the carboxylic acid function and then amidating these derivatives with an amine VIII.

In addition to halides, in particular the chlorides and the bromides, other activated forms of the carboxylic acid are, for example, imidazolides. The halides are generally preferred.

They are obtained by reacting carboxylic acids IXa–d with a halogenating agent, such as thionyl chloride, thionyl bromide, phosphorus oxychloride or -bromide, phosphorus tri- or pentachloride or -bromide, phosgene or elemental chlorine or bromine.

The halogenating agent is used in an amount of from 1 to 5, preferably from 1 to 2, mol. equivalents.

The reaction takes place at from 20° C. to the boiling point of the halogenating agent or, if an inert organic solvent is present, to its boiling point.

Examples of suitable solvents are hydrocarbons and halohydrocarbons, such as benzene, toluene and dichloromethane.

The activated carboxylic acid derivatives are usually isolated, for example by distilling off the halogenating agent and, where present, the solvent, before being reacted with the amines VIII.

In this case, the amidation is carried out at from $-20°$ to 50° C., preferably from 0° to 30° C., in an inert aprotic polar organic solvent.

Halohydrocarbons, such as dichloromethane, and ethers, such as diethyl ether and tert-butyl methyl ether, are particularly suitable solvents for this reaction.

Since a hydrogen halide is formed in the amidation of acyl halides, it is advisable to add the amine VIII in an excess of from 2 to 5, preferably from 2 to 3, mol. equivalents. If the amine is used in equimolar amounts (from 1 to 1.2 mol. equivalents), it is advantageous to add a base, in particular a tertiary amine, such as triethylamine or pyridine, to bind the hydrogen halide.

Reaction step B

The carboxylation of the carboxamides Xa-d is carried out, as a rule, at from $-100°$ to $+20°$ C., preferably from $-80°$ to $-400°$ C., in an aprotic polar inert organic solvent in the absence of moisture and in the presence of a base.

Carbon dioxide is a preferred carboxylating agent.

Particularly suitable solvents are ethers, such as diethyl ether, tert-butyl methyl ether, tetrahydrofuran and dioxane.

Preferably used bases are alkali metal hydrocarbons, such as methyllithium, n-butyllithium, tert-butyllithium and phenyllithium.

The reaction is usually carried out by a procedure in which 1.3 to 2.5 mol. equivalents of the dissolved base are first added to a solution of the carboxamide (Xa-d), and the resulting carboxamide derivative metallized in the ring reacts to give the desired product II-V when the electrophilic carboxylating reagent is subsequently added.

The carboxylic acids IXa-d required for this process are known from the literature or can be prepared by general methods from the literature, for example by oxidation of the corresponding alcohols or aldehydes or by hydrolysis of the corresponding nitriles (Beilstein, main work and 1st to 5th Supplement, Volume 18; The Chemistry of Heterocyclic Compounds, Interscience Publishers, New York, 1976, John Wiley & Sons, Inc., 1988, Vol. 44, Part I-III).

Processes for the preparation of the compounds XI and XII in which $R^2$ or $R^3$ is halogen and R, is alkyl:

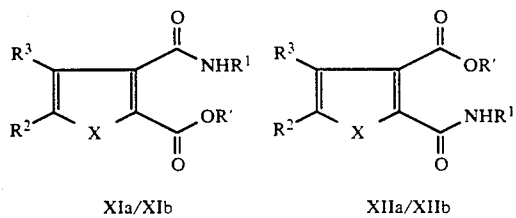

XIa/XIb     XIIa/XIIb ($R^2$ or $R^3$ = halogen and R' = alkyl)

These compounds XI and XII are obtained by diazotizing a dicarboxylic diester of the general formula XIII or XIV in a conventional manner, converting the diazotized compound with an inorganic halide into the corresponding derivative XV or XVI, then amidating the latter with an amine of the formula VIII and separating the resulting mixture of the isomeric compounds XIa and XIb or XIIA and XIIB into the individual components.

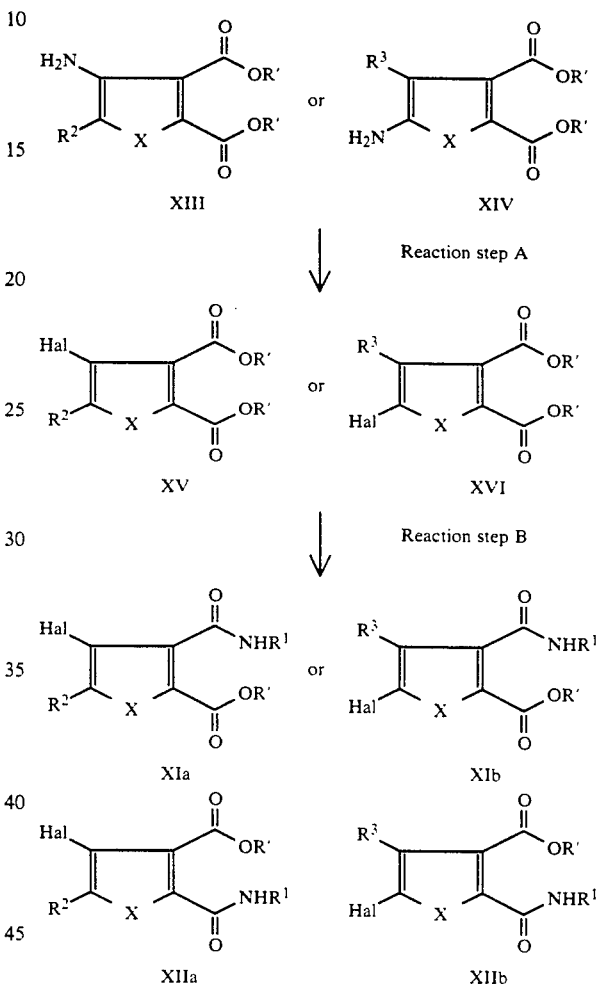

(R' = alkyl, Hal = fluorine, chlorine, bromine or iodine)

The reaction steps of this synthesis sequence can be carried out in general as follows:

Reaction step A

The diazotization of the dicarboxylic esters of the general formula XIII or XIV can be carried out, as a rule, at from $-20°$ to $+20°$ C., preferably from $-5°$ to $+10°$ C., in a mineral acid, in particular hydrochloric acid, in the presence of an alkali metal nitrite, such as sodium nitrite.

The diazonium salt thus obtained is then reacted in situ with from 1 to 5, preferably from 1.5 to 2.5, moles of an inorganic halide, in particular a copper(I) halide.

The reaction conditions can be varied within the limits of the process known for the Sandmeyer reaction (also see Houben-Weyl, Vol. X/3, page 1-211 (1965) and Chem. Zvesti 36 (1982), 401).

Reaction step B

The reaction of the resulting dicarboxylic esters XV or XVI with the amine VIII is carried out in general and in particular under conditions similar to those described for the process below.

However, solvents used here are in particular halohydrocarbons, such as methylene chloride, and ethers, such as diethyl ether, tert-butyl methyl ether and tetrahydrofuran.

The amine VIII is used in general in an equimolar amount or in excess, preferably in an amount of from 1 to 1.2 mol. equivalents, based on XV or XVI.

In this process, the isomeric carboxamides of the formulae XIa/b or XIIa/b are formed in different amounts. The isomer mixture is separated either by fractional crystallization or by chromatography.

The dicarboxylic diesters XIII required for this process are known or can be prepared from the corresponding oxo esters XVII, for example under conditions similar to those described in Synthesis, 1977, 200, according to the following equation:

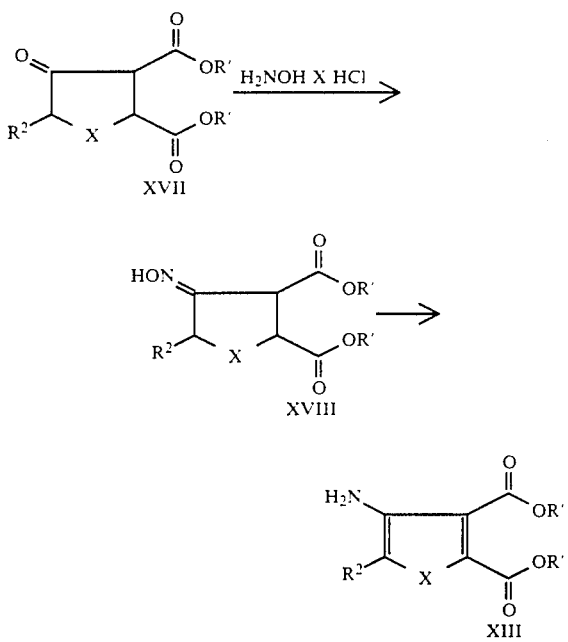

Processes for the preparation of compounds II and III

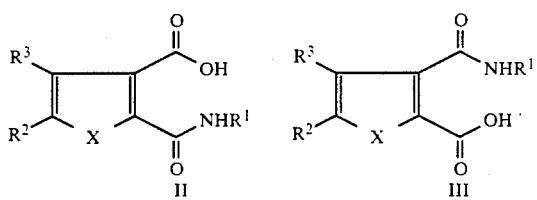

These carboxamides II or III are obtained, for example, by hydrolyzing a corresponding carboxamide of the formula XIa/b or XIIa/b, where $R^1$ is alkyl, in a conventional manner with an aqueous base.

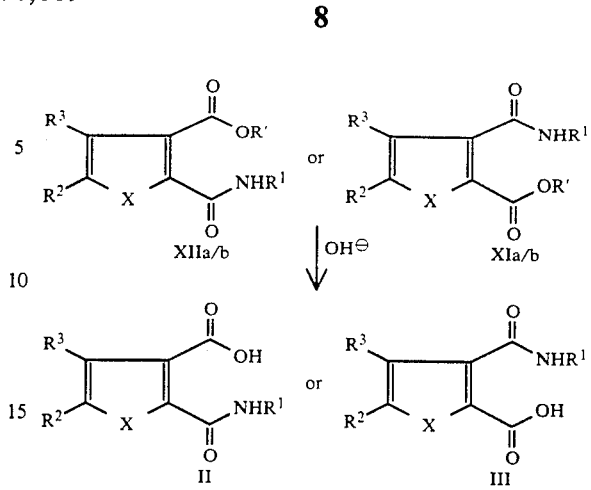

The reaction is carried out by a procedure in which a carboxamide XIa/b or XIIa/b ($R'$=alkyl) in an inert solvent is initially taken and is reacted with an aqueous base at from $-30°$ to $120°$ C., preferably from $-10°$ to $40°$ C. The carboxamides of the formula II or formula III ($R'$=H) are then liberated at from $-30°$ to $100°$ C., preferably from $-10°$ to $10°$ C., by adding a mineral acid.

Suitable solvents for this ester cleavage are alcohols, such as reethanol, ethanol, propanol or ethylene glycol; particularly preferably, the reaction is carried out in the alcohol corresponding to the ester component R'OH. The concentration of the educt XI or XII is in general from 0.1 to 5.0, preferably from 0.2 to 2.0, mol/l.

The aqueous base used is an aqueous solution of an alkali metal or alkaline earth metal hydroxide, such as LIOH, NAOH, KOH, Ca(OH)$_2$ or Ba(OH)$_2$, preferably NaOH or KOH. The hydroxides are used in the form of a 5-20% strength aqueous solution.

The molar ratios in which ester XI or XII and hydroxides are used are, for example, from 1:0.95 to 1:1 for alkali metal hydroxides and from 1:0.48 to 1:0.55 for alkaline earth metal hydroxides.

Another possible method for obtaining the dicarboxylic acid monoamides required as starting materials is to react dicarboxylic anhydrides of the general formula VI or VII in a conventional manner with an amine VIII and to separate the resulting positional isomers by chromatography or by fractional crystallization.

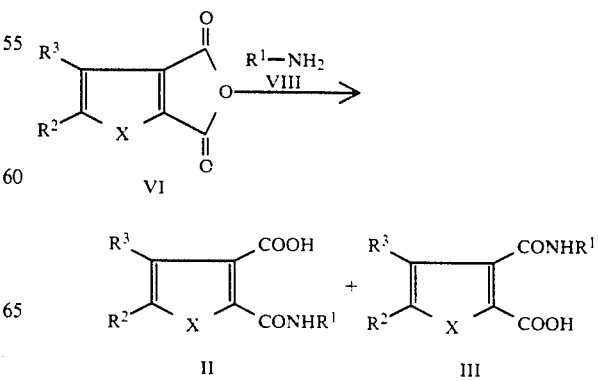

-continued

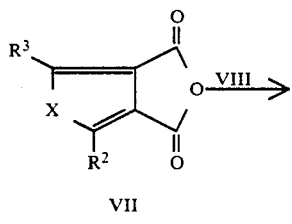

VII

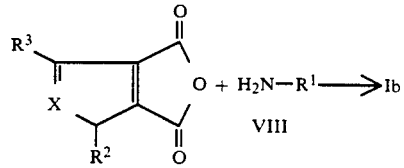

VII

In view of the intended use of the compounds IA and IB, suitable substituents are the following radicals:

X is oxygen or sulfur;

$R^1$ is hydrogen, hydroxyl;

$C_3$–$C_8$-cycloalkyl, such as cyclopropyl, cyclobutyl, cyclopentyl, cyclohexyl, cycloheptyl or cyclooctyl, in particular cyclopropyl, cyclobutyl, cyclopentyl or cyclohexyl, which may carry from one to three of the following radicals: halogen, such as fluorine, chlorine, bromine or iodine, in particular fluorine or chlorine, alkyl, such as methyl, ethyl, propyl, 1-methylethyl, butyl, 1-methylpropyl, 2-methylpropyl or 1,1-dimethylethyl, in particular methyl or ethyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular trifluoromethyl, alkoxy, such as methoxy, ethoxy, n-propoxy, 2-methylethoxy, n-butoxy, 1-methylpropoxy, 2-methylpropoxy or 1,1-dimethylethoxy, in particular methoxy or ethoxy, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy; $C_1$–$C_6$-alkyl as stated above, and pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, in particular methyl, ethyl, 1-methylethyl and 1,1-dimethylethyl, which may carry from one to three of the following radicals: hydroxyl, halogen as stated above, in particular fluorine or chlorine, cyano, cycloalkyl as stated above, in particular cyclopropyl, alkoxy as stated above, in particular methoxy or ethoxy, haloalkoxy as stated above, in particular trifluoromethoxy, alkylthio, such as methylthio, ethylthio, n-propylthio, 1-methylethylthio, n-butylthio, 1-methylpropylthio, 2-methylpropylthio or 1,1-dimethylethylthio, in particular methylthio or ethylthio, haloalkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio, alkylamino, such as methylamino, ethylamino, propylamino or isopropylamino, in particular methylamino, dialkylamino, such as dimethylamino, diethylamino, dipropylamino,

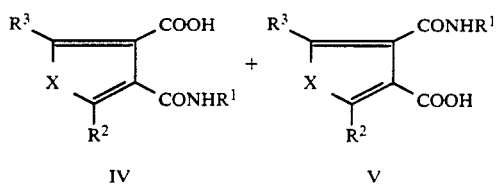

IV                    V

The reaction is carried out, as a rule, at from $-10°$ to $100°$ C., preferably from $0°$ to $30°$ C., in an inert organic solvent.

Suitable solvents are ethers, such as methyl tert-butyl ether, 1,2-dimethoxyethane, diethylene glycol dimethyl ether, tetrahydrofuran or dioxane.

The concentration of the educts in the solvent is in general from 0.1 to 5, preferably from 0.2 to 2, mol/l.

The molar ratio of VI or VII to VIII is in general from 1:5 to 1:1, preferably from 1:2 to 1:1.

The dicarboxylic anhydrides VI or VII which are required are known or can be prepared in a conventional manner by reacting the corresponding dicarboxylic acids with the anhydride of a lower carboxylic acid, in particular acetic anhydride.

Method B

In another process for the preparation of compounds of the formulae Ia and Ib, the dicarboxylic anhydride of the formula VI or VII is reacted with an amine of the formula VIII. The reaction is advantageously carried out by a procedure in which the anhydride VI or VII in a solvent is heated at $0°$–$150°$ C., preferably $20°$–$100°$ C. Examples of suitable solvents are lower alkanoic acids, such as acetic acid, propionic acid or isobutyric acid, and esters of these acids, such as ethyl acetate, as well as aprotic solvents, such as toluene or xylene, and/or dimethylformamide. When the reaction is carried out in an aprotic solvent, it is advisable to add acidic catalysts, for example aromatic sulfonic acids, and to remove the water of reaction continuously. The molar ratios in which the required starting compounds are reacted with one another are in general from 0.9 to 5, preferably from 0.9 to 1.5, for the ratio of anhydride to amine.

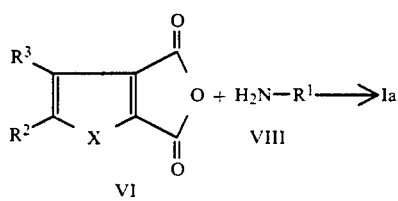

VI diisopropylamino or methylethylamino, in particular dimethylamino, cycloalkylamino, such as cyclopropylamino, cyclobutylamino, cyclopentylamino or cyclohexylamino, in particular cyclopropylamino, and/or a radical

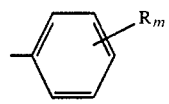

where R is cyano, nitro, halogen, in particular fluorine or chlorine, $C_1-C_4$-alkyl, in particular methyl, ethyl or 1-methylethyl, $C_1-C_4$-haloalkyl, in particular $C_1$- or $C_2$-haloalkyl, especially trifluoromethyl, $C_1-C_4$-dlkoxy, in particular methoxy, ethoxy or 1-methylethoxy $C_1-C_4$-haloalkoxy, in particular difluoromethoxy or trifluoromethoxy, $C_2-C_4$-alknyloxy, such as proparcjyloxyl $C_1-C_4$-alkylthio, in particular methylthio or ethylthio, $C_1-C_4$-haloalkylthio, in particular difluoromethylthio or trifluoromethylthio, $C_1-C_4$-alkoxycarbonylalkoxy, in particular methoxy- or ethoxycarbonylmethoxy, $C_1-C_4$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, in particular methoxycarbonyl or ethoxycarbonyl, 2-alkoxycarbonylprop-1-enyl, $C_1-C_4$-alkanoyl, such as acetyl, $C_1-C_4$-haloalkanoyl, such as trifluoro- or trichloroacetyl, and formyl, protected formyl, such as dioxolanyl, and/or phenyl, and m is 0, 1, 2 or 3, and the radicals R may be different when m is 2 or 3;

$C_1-C_4$-alkoxy, in particular methoxy or ethoxy;

$C_2-C_6$-cyanoalkyl, such as cyanomethyl, cyanobutyl, 2-cyano-3-methylbut-2-yl and in particular 1,1-dimethylcyanometh yl or 1,1-diethylcyanomethyl;

$C_3-C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, particularly preferably 2-propenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, i-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynynl, i-ethyl-2-butynyl, 1-ethyl-3-butynyl, 2-ethyl-3-butynyl and 1-ethyl-1-methyl-2-propynyl, in particular 2-propynyl;

phenyl and naphthyl, where these groups may carry from one to three of the radicals stated in general and in particular for R, e.g. 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-trifluoromethylphenyl, 3-trifluoromethylphenyl or 4-trifluoromethylphenyl;

a 5-membered or 6-membered heterocyclic structure containing one or two hetero atoms selected from the group consisting of nitrogen, oxygen and sulfur, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-iso-xazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 4-pyrrolyl, 3-pyrazolyl, 4-pyrazolyl, 5-pyrazolyl, 2-pyridyl, 3-pyridyl, 4-pyridyl or 2-(4,6-dimethylpyrimidinyl), where this ring may carry one or two of the following radicals: halogen, alkyl, haloalkyl, alkoxy, haloalkoxy and/or alkylthio as stated in general and in particular for $R^1$, or di-$C_1-C_4$-alkylamino, in particular dimethyl- or diethylamino;

$R^2$ and $R^3$ are each nitro; cyano;

halogen, in particular fluorine, chlorine or bromine; amino which may carry one or thio $C_1-C_4$-alkyl groups as stated for $R^1$, in particular methyl or ethyl, and/or a $C_1-C_4$-alkylcarbonyl group, such as methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl, in particular methylcarbonyl or ethylcarbonyl;

$C_1-C_4$-alkoxy or alkylthio, in particular methoxy, ethoxy, methylthio or ethylthio, where these groups may carry from one to nine halogen atoms, in particular fluorine or chlorine, e.g. difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy or trifluoromethylthio;

$C_2-C_6$-alkenyl, such as ethenyl, 1-propenyl, 1-methylethenyl, 1-butenyl, 1-methyl-1-propenyl, 2-methyl-1-propenyl, 1-pentenyl, 1-methyl-1-butenyl, 2-methyl-1-butenyl, 1,1-dimethyl-1-propenyl, 1-ethyl-1-propenyl, 1-hexenyl, 1-methyl-1-pentenyl, 2-methyl-1-pentenyl, 3-methyl-1-pentenyl, 4-methyl-1-pentenyl, 1,2-dimethyl-1-butenyl, 1,3-dimethyl-1-butenyl, 2,3-dimethyl-1-butenyl, 3,3-dimethyl-1-butenyl, 1-ethyl-1-butenyl, 2-ethyl-1-butenyl or 1-ethyl-2-methyl-1-propenyl, in particular 2-propenyl; $C_2-C_6$-alkynyl, such as ethynyl, 1-propynyl, 1-butynyl, 1-pentynyl, 1-methyl-3-butynyl, 1-hexynyl, 3-methyl-1-pentynyl, 4-methyl-1-pentynyl or 3,3-dimethyl-1-butynyl, in particular 2-propynyl;

$C_1-C_4$-alkyl- or haloalkylsulfonyl, in particular methylsulfonyl, trifluoromethylsulfonyl or trichloromethylsulfonyl;

phenyl, phenoxy or phenylthio, where these groups may carry from one to three of the radicals stated in general and in particular for R, such as 2-fluorophenyl, 3-fluorophenyl, 4-fluorophenyl, 2-chlorophenyl, 3-chlorophenyl, 4-chlorophenyl, 2-methoxyphenyl, 3- methoxyphenyl, 4-methoxyphenyl, 2-trifluoromethylphenyl, 3-trifluoromethylphenyl or 4-trifluoromethylphenyl,
or one of the groups stated in general and in particular for R¹.
Examples of herbicidal compounds of the formulae Ia and Ib are shown specifically below:
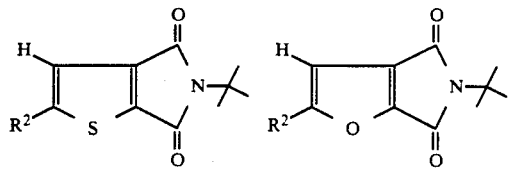
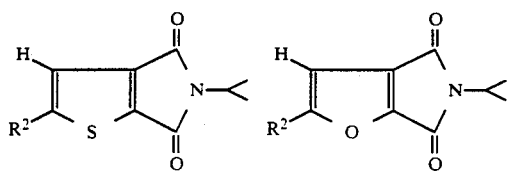
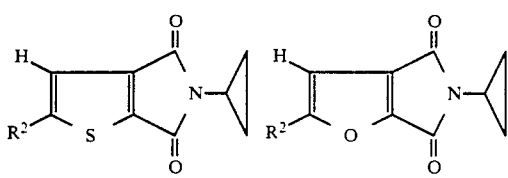
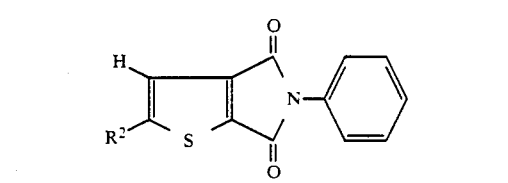
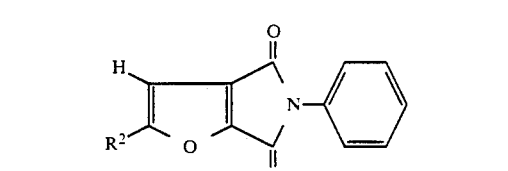
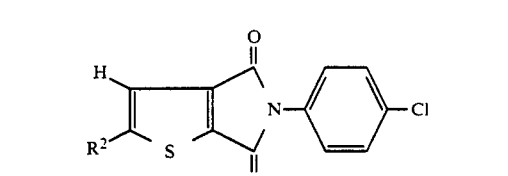
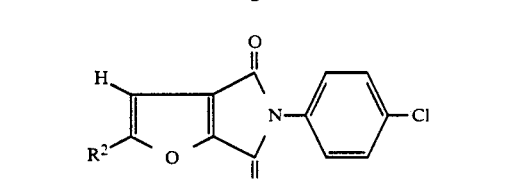
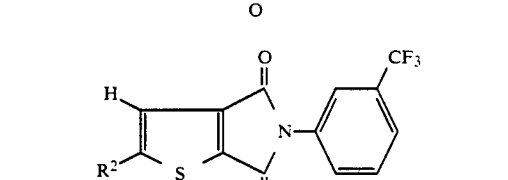
-continued
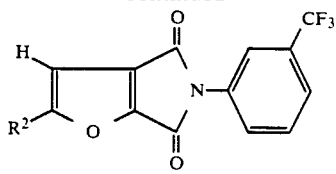
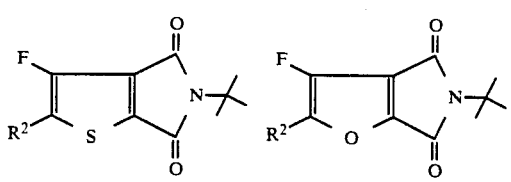
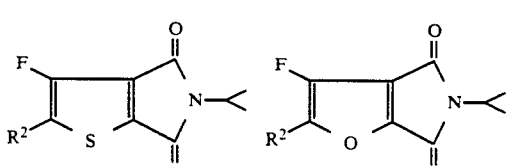
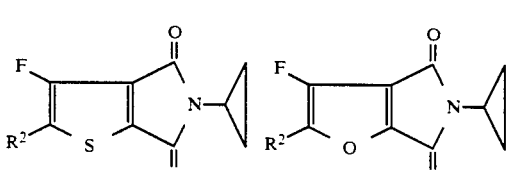
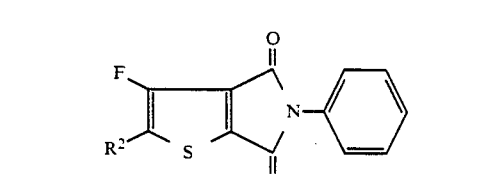
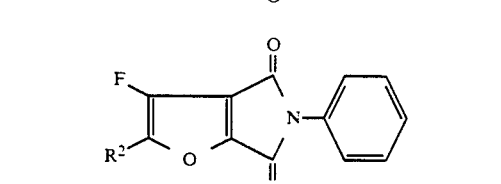
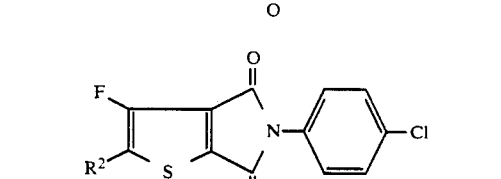
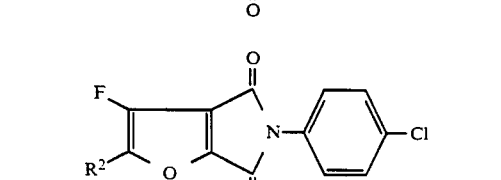
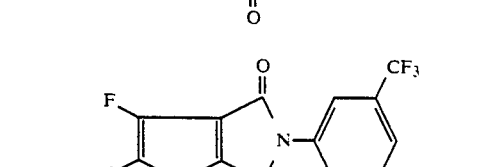

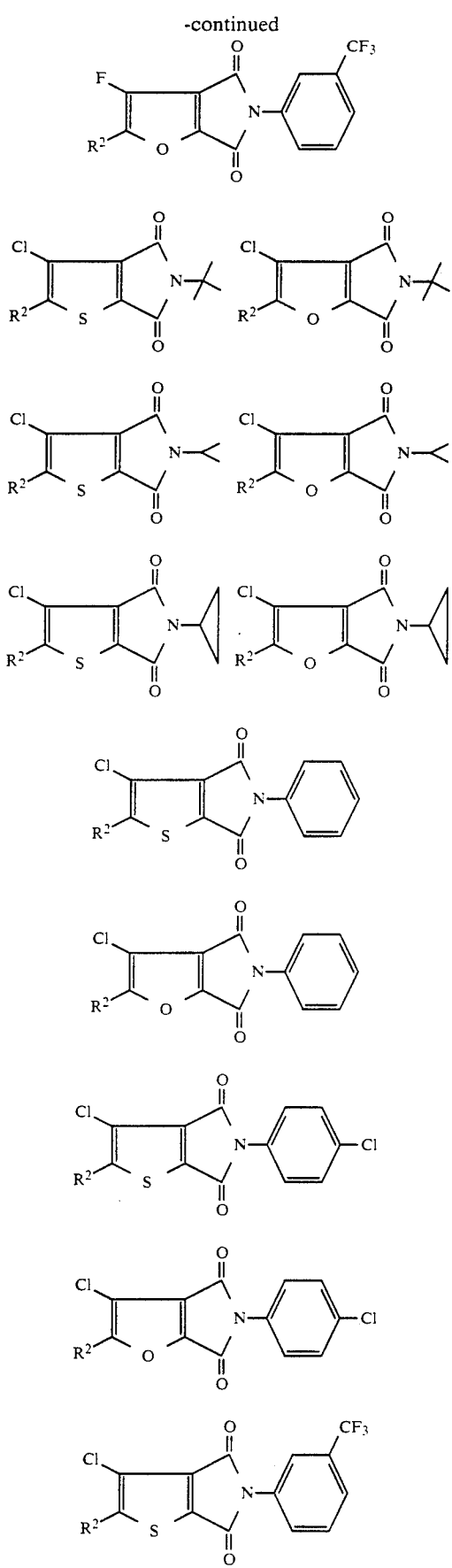

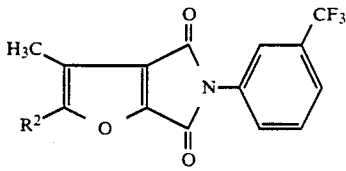
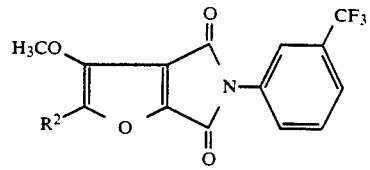
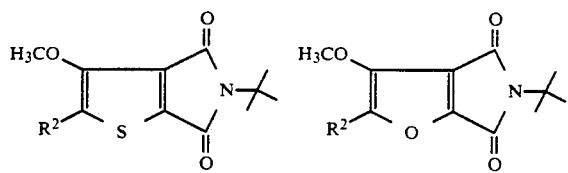
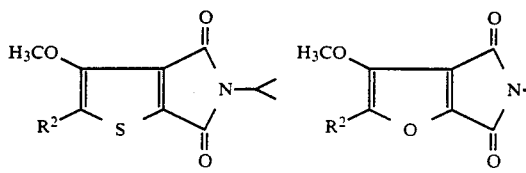
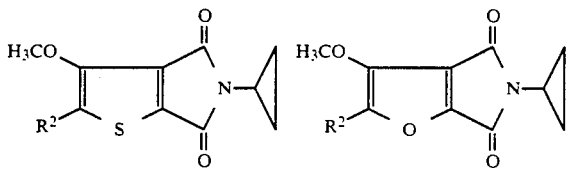
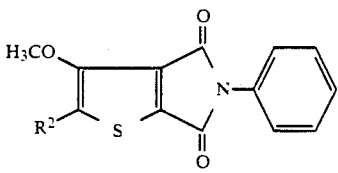
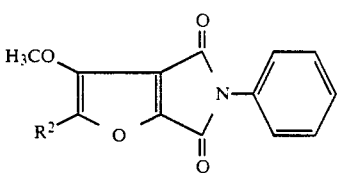
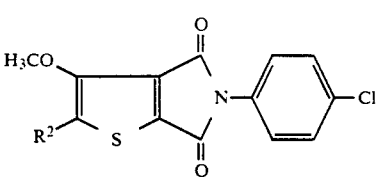
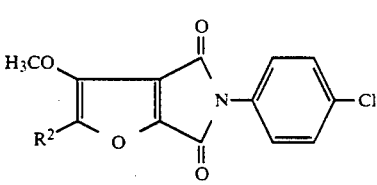
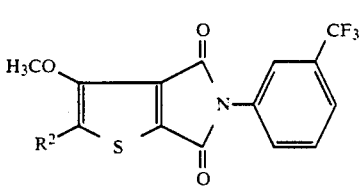

where $R^2$ in each case has one of the following meanings: hydrogen, fluorine, chlorine, bromine, iodine, cyano, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl.

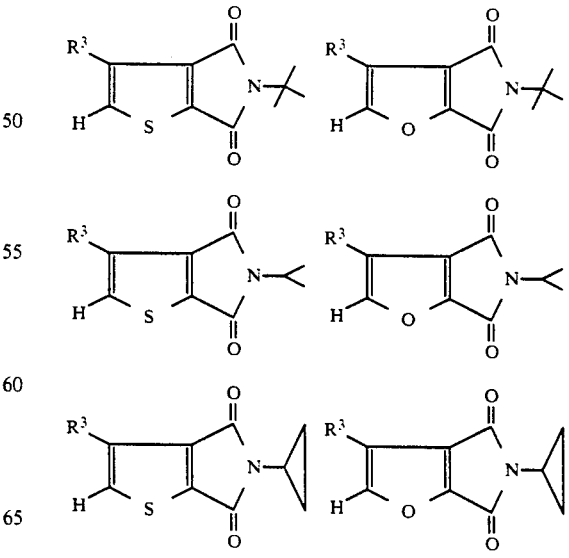

-continued
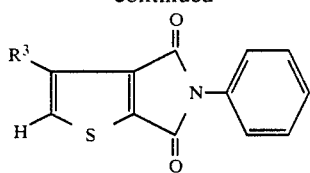
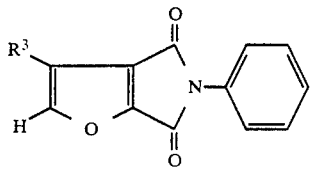
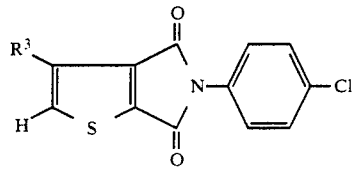
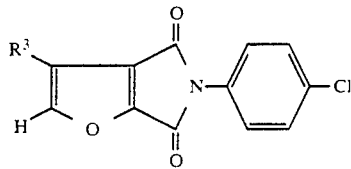
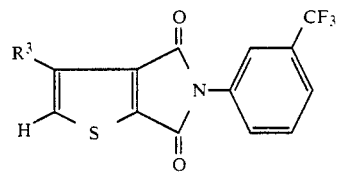
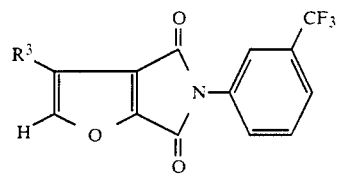
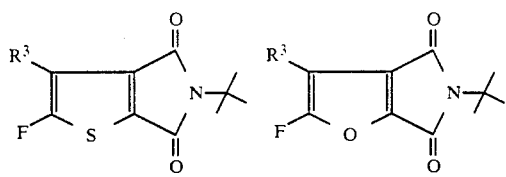
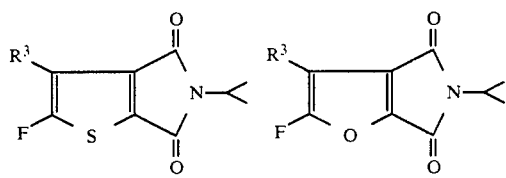
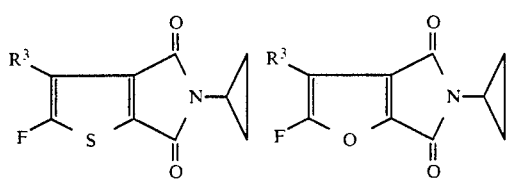
-continued
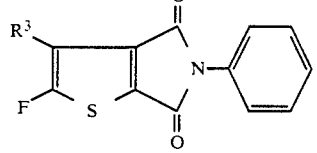
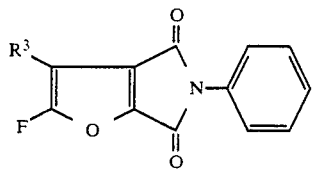
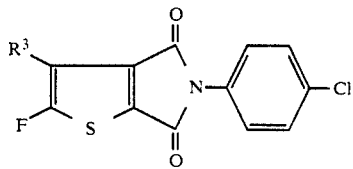
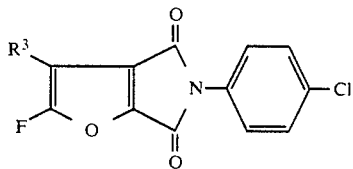
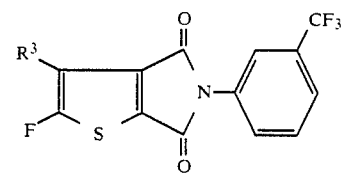
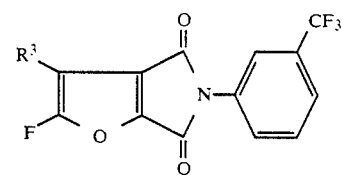
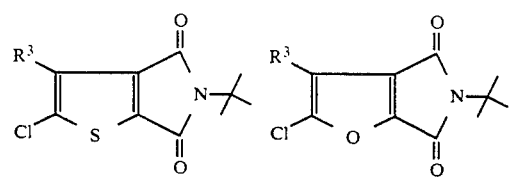
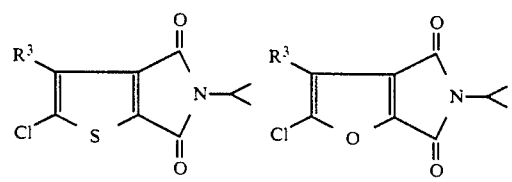
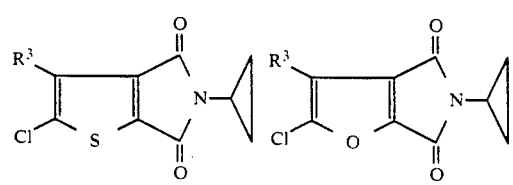

-continued

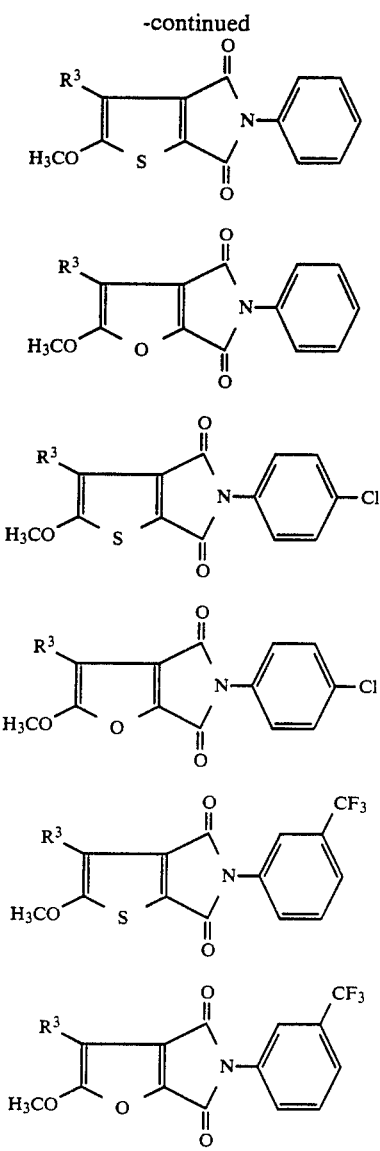

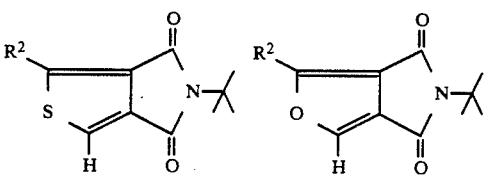
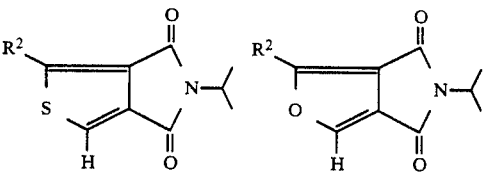
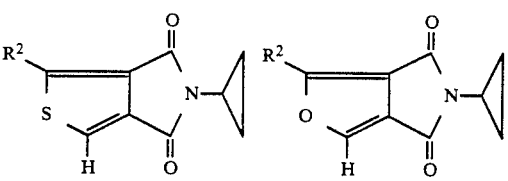
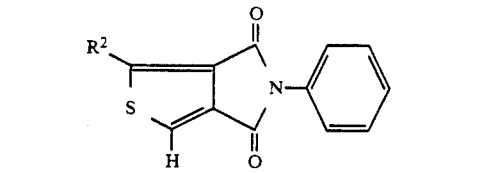
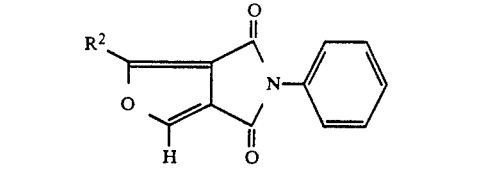
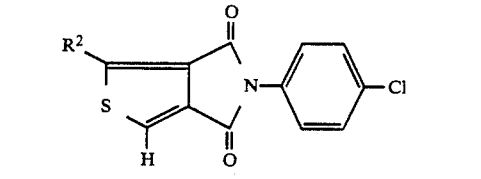
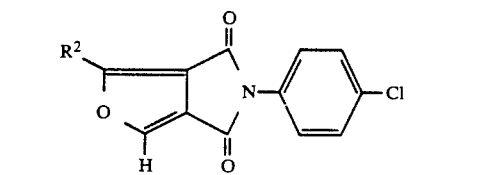

where R³ in each case has one of the following meanings: hydrogen, fluorine, chlorine, bromine, iodine, cyano, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl.

5,276,009
25
-continued
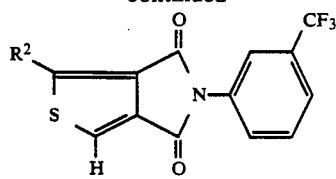
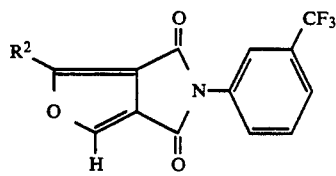
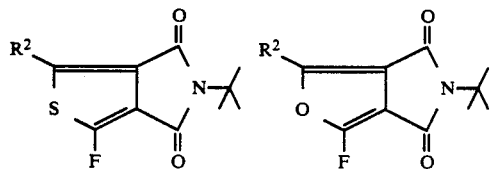
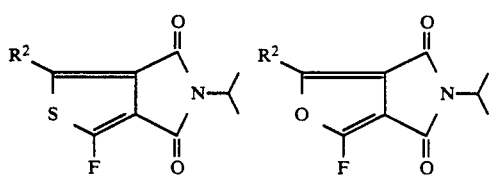
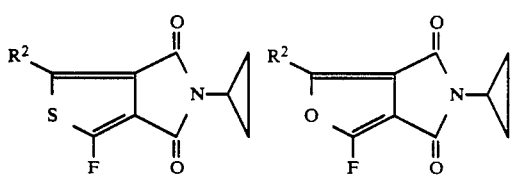
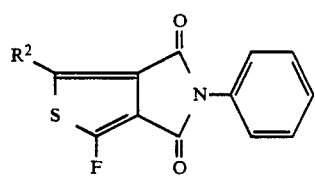
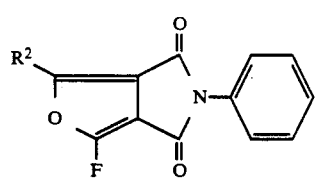
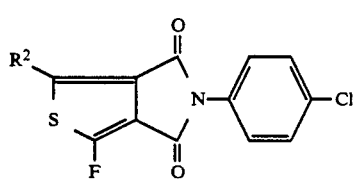
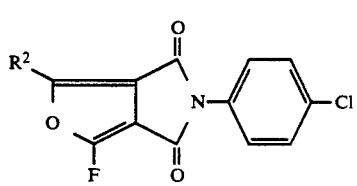
26
-continued
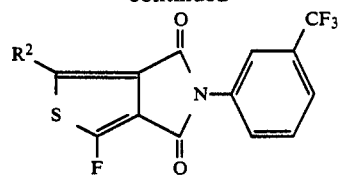
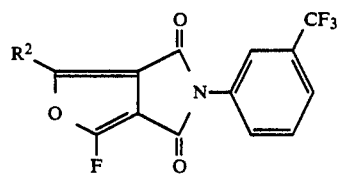
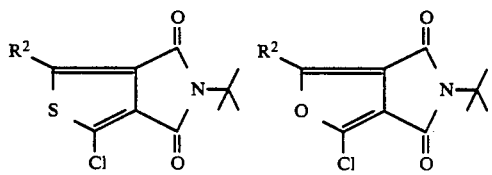
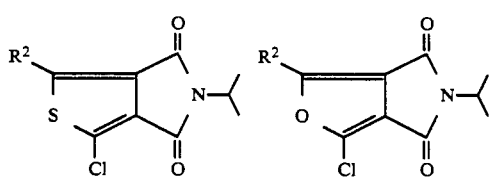
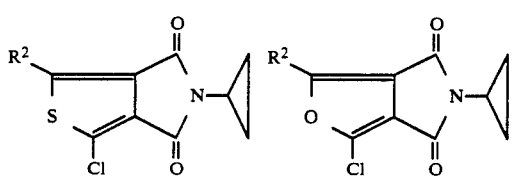
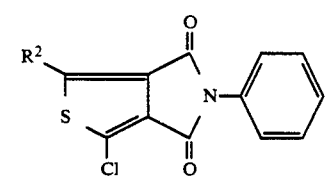
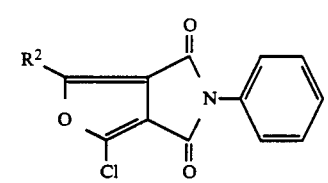
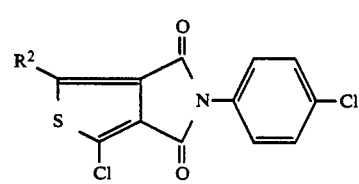
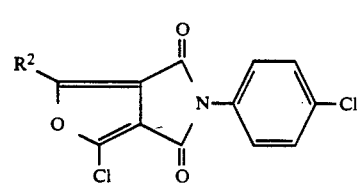

-continued

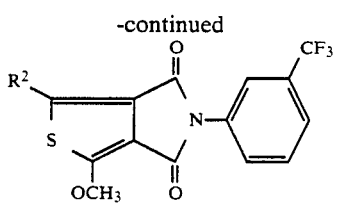

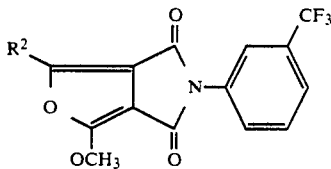

where R² in each case has the following meanings: hydrogen, fluorine, chlorine, bromine iodine, cyano, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorphenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl.

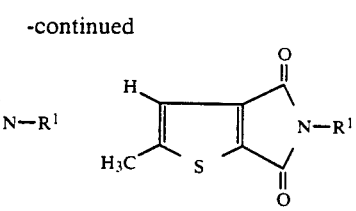

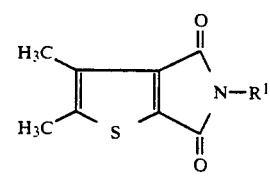

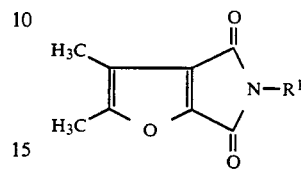

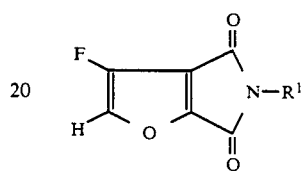

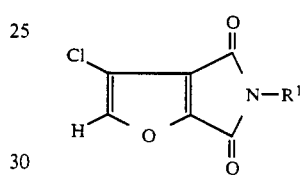

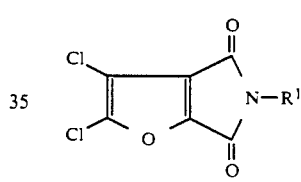

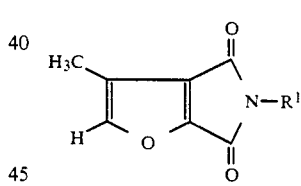

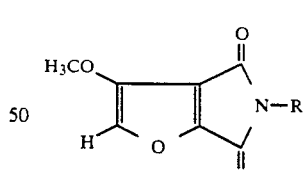

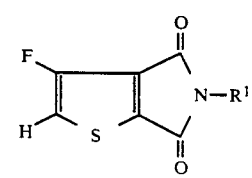

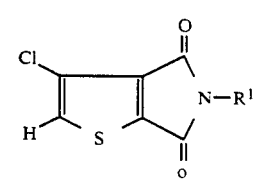

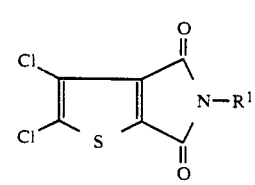

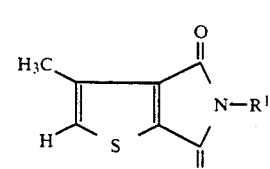

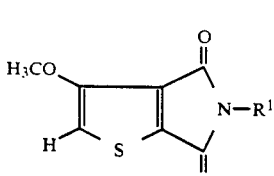

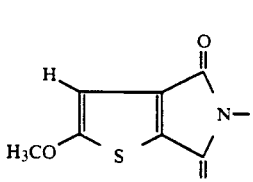

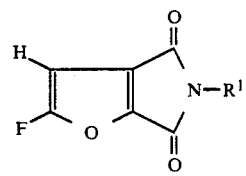

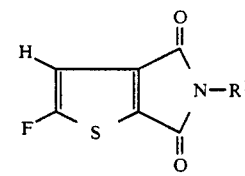

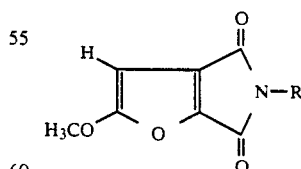

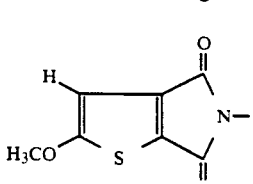

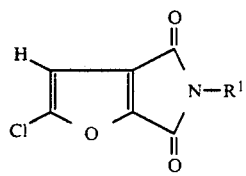

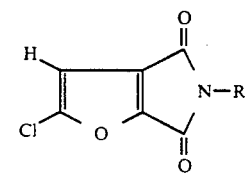

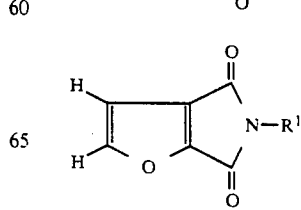

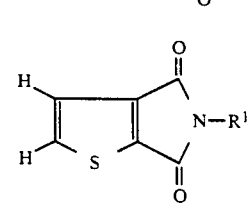

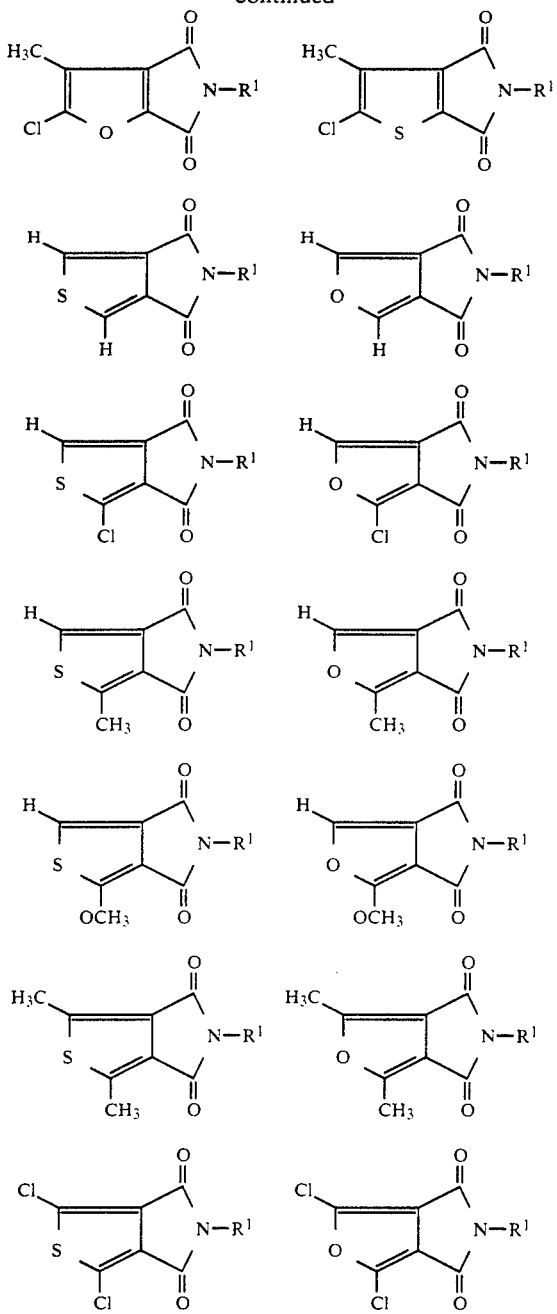

where R¹ in each case has the following meanings: methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, 1-methylcyclohexyl, 1-ethylcyclohexyl, cyclohexylmethyl, 2-propenyl, 1-methyl-2-propenyl, 1, 1-dimethyl-2-propenyl, 2-propynyl, 1-methyl-2-propynyl, 1,1-dimethylpropynyl, phenylmethyl, 1-methylphenylmethyl, 1, 1-dimethylphenylmethyl, 2-phenylethyl, 2-methylthioethyl, 1-methyl-2-methylthioethyl, 1,1-dimethyl-2-methylthioethyl, 3-methylthiopropyl, 2-fluoroethyl, 2-fluoro-1-methylethyl, 1,1-dimethyl-2-fluoroethyl, 2-chloroethyl, 2-chloro-1-methylethyl, 2-chloro-1,1-dimethylethyl, 2-methoxyethyl, 2-methoxy-1-methylethyl, 1,1-dimethyl-2-methoxyethyl, 3-methoxypropyl, 2-cyanoethyl, 2-cyano-1-methylethyl, 2-cyano-1,1-dimethylethyl, dimethylamino, diethylamino, morpholino, piperidino, phenyl, 2-methylphenyl, 3-methylphenyl, 4-methylphenyl, 2-ethylphenyl, 3-ethylphenyl, 4-ethylphenyl, 2,3-dimethylphenyl, 2,4-dimethylpheny, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,4,5-trimethylphenyl, 2,4,6-trimethylphenyl, 3,4,5-trimethylphenyl, 2-trifluoromethylphenyl, 3-trifluoromethylphenyl, 4-trifluoromethylphenyl, 2-fluorophenyl, 3-fluorophenyl, 4-fluorophenyl, 2-chlorophenyl, 3-chlorophenyl, 4-fluorophenyl, 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,4,6-trichlorophenyl, 3,4,5-trichlorophenyl, 2-cyanophenyl, 3-cyanophenyl, 4-cyanophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4,5-dimethoxyphenyl, 2-trifluoromethoxyphenyl, 3-trifluoromethoxyphenyl, 4-trifluoromethoxyphenyl, 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,4-dinitrophenyl, 3,5-dinitrophenyl, 1-naphthyl, 2-naphthyl, 3-tetrahydrofuryl, 4-tetrahydropyranyl or 2-thiazolyl.

In the furan- or thiophen-2,3- or 3,4-dicarboxamides, the abovementioned definitions of R¹ and R² can moreover be combined with one another to give combinations other than the stated ones.

Suitable salts of the compounds of the formulae Ia and Ib are agriculturally useable salts, for example alkali metal salts, such as the potassium or sodium salt, alkaline earth metal salts, such as the calcium, magnesium or barium salt, manganese, copper, zinc and iron salts and ammonium, phosphonium, sulfonium or sulfoxonium salts, for example ammonium salts, tetraalkylammonium salts, benzyltridlkylammonium salts, trialkylsulfonium salts or trialkylsulfoxonium salts.

The novel herbicidal compounds or the agents containing them can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds are suitable in general for the preparation of directly sprayable solutions, emulsions, pastes or oil dispersions. Suitable inert additives are mineral oil fractions having a medium to high boiling point, such as kerosene or diesel oil, and coal tar oils and oils of vegetable or animal origin, aliphatic, cyclic and aromatic hydrocarbons, e.g. ene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or in solution in an oil or solvent, can be homogenized in water by means of wetting agents, adhesives, dispersants or emulsifiers. However, it is also possible to prepare concentrates which consist of active substance, wetting agents, adhesives, dispersants or emulsifiers and possibly a solvent or oil and which are suitable for dilution with water.

Suitable surfactants are the alkali metal, alkaline earth metal and ammonium salts of aromatic sulfonic acids, eg. lignin-, phenol-, naphthalene- and dibutylnaphthalenesulfonic acid, and of fatty acids, alkylsulfonates, alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenyl ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as cereal meal, ground bark, woodmeal and nutshell meal, cellulose powder or other solid carriers.

The formulations contain from 0.1 to 95, preferably from 0.5 to 90% by weight of active ingredient. The active ingredients are used in a purity of from 90 to 100%, preferably from 95 to 100% (according to NMR spectrum).

The novel compounds I can be formulated, for example, as follows:

I. 90 parts by weight of compound No. 1.005 are mixed with 10 parts by weight of N-methyl-α-pyrrolidone, and a solution which is suitable for use in the form of very small drops is obtained.

II. 20 parts by weight of compound No. 2.007 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 2.007 are dissolved in a mixture which consists of 40 parts by weight of cyclohexanone, 30 parts by weight of isobutanone, 20 parts by weight of the adduct of 7 moles of ethylene oxide with 1 mole of iso-octylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 1.005 are dissolved in a mixture which consists of 25 parts by weight of cyclohexanone, 65 parts by weight of a mineral oil fraction boiling within the range from 210° to 280° C. and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of active ingredient No. 2.007 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1.005 are mixed with 97 parts by weight of finely divided kaolin. A dusting agent which contains 3% by weight of the active ingredient is obtained in this manner.

VII. 30 parts by weight of active ingredient No. 2.007 are thoroughly mixed with a mixture of 92 parts by weight of silica gel powder and 8 parts by weight of liquid paraffin, which was sprayed onto the surface of the silica gel. A formulation of the active ingredient having good adhesion is obtained in this manner.

VIII. 20 parts by weight of active ingredient No. 1.005 are thoroughly mixed with 2 parts by weight of the calcium salt of dodecylbenzenesulfonic acid and 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients can be applied by the preemergence or postemergence method. If the active ingredients are less well tolerated by certain crops, it is possible to use application methods in which the herbicides are sprayed with the aid of the sprayer in such a way that the leaves of the sensitive crops remain as far as possible unaffected while the active ingredients reach the leaves of undesirable plants growing underneath or the uncovered soil surface (post-directed, lay-by).

The application rates of the active ingredient for use as herbicides are from 0.001 to 3, preferably from 0.01 to 2, kg/ha of active substance, depending on the aim of control, the season, the target plants and the stage of growth.

In view of the available action spectrum for weed control, the tolerance by crops or the desired effect on the growth thereof, and in view of the variety of application methods, the novel compounds can be used in a large number of crops. For example, the following crops are suitable:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica rapa var. silvestris | beets |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus dulcis | almond trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (S. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To extend the action spectrum and to achieve synergistic effects, the compounds of the formula I can be mixed with one another and with members of other groups of herbicidal or growth-regulating active ingredients and applied together with these. Examples of suitable components of the mixture are diazine, 4H-3,1-benzoxazine derivatives, benzothiadiazinones, 2,6-dinitroanilines, N-phenylcarbamates, thiocarbamates, halocarboxylic acids, triazines, amides, ureas, diphenyl ether, triazinones, uracils, benzofuran derivatives, cyclohexane-1,3-dione derivatives, quinolinecarboxylic acid derivatives, sulfonylurea derivatives, (het)aryloxyphenoxypropionic acids, salts, esters and amides thereof and others.

It may also be useful to apply the compounds, alone or in combination with other herbicides, also as a mixture with further crop protection agents, for example with pesticides, agents for controlling phytopathogenic fungi or bactericides. The miscability with mineral salt solutions which are used for eliminating nutrient and trace element deficiencies is also of interest. It is also possible to add nonphytotoxic oils or oil concentrates.

The Examples which follow illustrate the preparation of the compounds Ia and Ib and their intermediates II to V.

Preparation of the intermediates

EXAMPLE 1

Thiophene-3,4-dicarboxylic anhydride

Thiophene-3,4-dicarboxylic acid (12 g, 0.07 mol) is dissolved in acetic anhydride (60 ml) and heated at the boil for 2.5 hours. The mixture is then evaporated to dryness. 10.55 g (98%) of thiophene-3,4-dicarboxylic anhydride (mp. 147° to 149° C.) are obtained.

EXAMPLE 2

4-(4-Chlorophenyl)-aminocarbonylthiophene-3-carboxylic acid

Thiophene-3,4-dicarboxylic anhydride (2 g, 0.013 mol) in 60 ml of toluene is initially taken and 4-chloroaniline (1.65 g, 0.013 mol) is added. Stirring is carried out for 3 hours at room temperature, and the precipitated carboxylic acid is filtered off, washed with a little toluene and dried to give 3.7 g (100%) of the desired product of melting point 204° to 208° C.

EXAMPLE 3

4-(4-Chlorophenyl)-aminocarbonylthiophene-3-carboxylic acid hydroxysuccinimide ester 4-(4-Chlorophenyl)-aminocarbonylthiophene-3-carboxylic acid (1.7 g, 0.006 mol) is dissolved in 60 ml of tetrahydrofuran, N-hydroxysuccinimide (0.7 g, 0.006 mol) and N,N-dicyclohexylcarbodiimide (1.25 g, 0.006 mol) are added and stirring is carried out for several hours at room temperature. The solution is then cooled at 0° C. for a few hours, the precipitated urea is filtered off under suction and the filtrate is evaporated to dryness. Yield: 1.8 g, 66%; mp. 65° to 67° C.

EXAMPLE 4

4-Chlorothiophene-3-carboxanilide

4-Chlorothiophene-3-carbonyl chloride (13.5 g, 0.075 mol) are dissolved in 30 ml of dioxane and the solution is added dropwise at room temperature to a solution of aniline (7.7 g, 0.083 mol) in pyridine (160 ml). Stirring is carried out for 12 hours at room temperature, after which the mixture is evaporated to dryness and the residue is taken up in dichloromethane. The organic phase is extracted with aqueous citric acid solution, sodium bicarbonate solution and water, dried and evaporated to dryness. Yield: 16.7 g, 94%; mp. 119° to 121° C.

EXAMPLE 5

4-Chloro-3-phenylaminocarbonylthiophene-2-carboxylic acid

4-Chlorothiophene-3-carboxanilide (14.6 g, 0.061 mol) is dissolved in 450 ml of tetrahydrofuran, the solution is cooled to −70° C. and n-butyllithium (0.13 mol, 1.6N solution in n-hexane) is added. After 30 minutes, carbon dioxide gas is passed in until the solution is saturated, and the solution is allowed to warm up slowly to room temperature. It is worked up by evaporating to dryness, taking up the solid residue in a mixture of water, sodium hydroxide solution and ethyl acetate, separating the phases and acidifying the aqueous phase with hydrochloric acid. The carboxylic acid is precipitated. Yield: 13.5 g, 78%; mp. 208° to 210° C.

For example, the dicarboxylic acid monoamides shown in Tables a to c were prepared by the methods described.

TABLE a

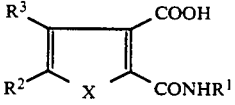

II

| $R^1$ | $R^2$ | $R^3$ | X | mp. (°C.) $^1$H-NMR (DMSO-$d_6$, δ in ppm) |
|---|---|---|---|---|
| —C(CH$_3$)$_2$CH$_2$CH$_3$ | H | H | S | 77–84 |
| —C(CH$_3$)$_3$ | H | H | S | 179–182 |
| —C(CH$_3$)$_2$CH=CH$_2$ | H | H | S | 98–100 |
| —C(C$_2$H$_5$)$_2$C≡CH | H | H | S | Oil |
| —C(CH$_3$)$_2$CN | H | H | S | 200–205 |
| —C(CH$_3$)$_2$CH$_2$SCH$_3$ | H | H | S | 108–112 |
| 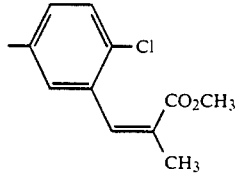 | H | H | S | 178–184 |
| 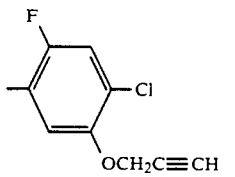 | H | H | S | 242–247 |
| 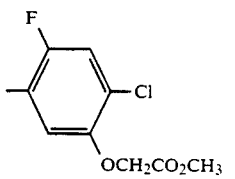 | H | H | S | 222–226 |
| —C(CH$_3$)$_3$ | CH$_3$ | H | S | 162–166 |
| —CH(CH$_3$)$_2$ | CH$_3$ | H | S | 88–90 |
| Cyclopropyl | CH$_3$ | H | S | 147–149 |
| 4-ClC$_6$H$_4$ | CH$_3$ | H | S | 230–235 |
| —C(CH$_3$)$_3$ | Cl | H | S | 233–235 |
| Cyclopropyl | Cl | H | S | 204–206 |
| —CH(CH$_3$)$_2$ | Cl | H | S | 175–177 |
| —C$_6$H$_5$ | Cl | H | S | 220–222 |
| 3-CF$_3$—C$_6$H$_4$ | Cl | H | S | 158–160 |
| —OC(CH$_3$)$_3$ | Cl | H | S | 206–208 |
| 3-CF$_3$—C$_6$H$_4$ | H | H | S | 151–153 |
| 4-Cl—C$_6$H$_4$ | H | H | S | 218–220 |
| 2,6-CH$_3$,CH$_3$—C$_6$H$_3$ | CH$_3$ | H | S | 237–239 |
| C$_6$H$_5$ | H | H | S | 258–260 |
| 2,4,6-CH$_3$,CH$_3$,CH$_3$—C$_6$H$_2$ | Cl | H | S | 246–248 |
| 3-CF$_3$—C$_6$H$_4$ | 4-CH$_3$—C$_6$H$_4$ | H | S | 255 |
| 2,6-C$_2$H$_5$,C$_2$H$_5$—C$_6$H$_3$ | Cl | H | S | 170–172 |
| Cyclopropyl | O—CH$_3$ | H | S | 168–170 |
| —C(CH$_3$)$_3$ | 4-CH$_3$—C$_6$H$_4$ | H | S | 144–146 |
| Cyclohexyl | Cl | H | S | 251–253 |
| —CH(CH$_3$)$_2$ | H | H | S | 141–143 |
| —C(CH$_3$)$_3$ | OCH$_3$ | H | S | 176–178 |
| —C(CH$_3$)$_3$ | H | H | O | 123–126 |
| —CH(CH$_3$)$_2$ | H | H | O | 62–70 |

TABLE a-continued

Structure II: R³ and COOH on one side, R² and CONHR¹ on the other side of ring containing X

| R¹ | R² | R³ | X | mp. (°C.) ¹H-NMR (DMSO-d₆, δ in ppm) |
|---|---|---|---|---|
| 3-CF₃—C₆H₄ | H | H | O | 170–173 |
| —C(CH₃)₃ | CH₃ | H | O | 124–127 |
| —CH(CH₃)₂ | CH₃ | H | O | 138–141 |
| Cyclopropyl | CH₃ | H | O | 154–160 |
| 4-Cl—C₆H₄ | CH₃ | H | O | 230–232 |
| 2-F—C₆H₄ | Cl | H | S | 230–232 |
| C₆H₅ | OCH₃ | H | S | 190–192 |
| 3-CF₃—C₆H₄ | OCH₃ | H | S | 3.85(s, 3H); 6.7(s, 1H); 7.35(d, 1H); 7.55(t, 1H); 7.8(d, 1H); 8.15(s, 1H) |
| C₆H₅ | CH₃ | H | S | 230–232 |
| 3-CF₃—C₆H₄ | CH₃ | H | S | 2.35(s, 3H); 7.15(s, 1H); 7.30(d, 1H); 7.50(t, 1H); 7.75(d, 1H); 8.15(s, 1H) |
| C₆H₁₁ | CH₃ | H | S | 219–221 |
| Cyclopropyl | 4-CH₃—C₆H₄ | H | S | 167–169 |
| 2,6-CH₃,CH₃—C₆H₃ | Cl | H | S | 2.15(s, 6H); 7.10(s, 3H); 7.50(s, 1H); 11.15(s, 1H); |
| —C(CH₃)₂CN | Cl | H | S | 219–221 |
| 4-Cl—C₆H₄ | OCH₃ | H | S | 212–214 |
| Cyclopropyl | C₂H₅ | H | S | 111–112 |
| —CH(CH₃)₂ | Cl | Cl | S | 194–196 |
| C₆H₅ | —C≡C—C₆H₅ | H | S | 7.20–7.80(m, 12H); 16.4(s, 1H) |
| Cyclopropyl | 2-Pyridyl | H | S | 204–205 |
| Cyclopropyl | Cl | Cl | S | 189–191 |
| Cyclopropyl | —C≡C—C₆H₅ | H | S | 194–196 |
| 1-Cyclopropyl-ethyl | Cl | H | S | 151–155 |
| 3-CF₃—C₆H₄ | CH₃ | H | O | 217–219 |

TABLE b

Structure III: R³ and CONHR¹ on one side, R² and COOH on the other side of ring containing X

| R¹ | R² | R³ | X | mp. (°C.) |
|---|---|---|---|---|
| —CH(CH₃)₂ | H | H | S | 160–162 |
| —C(CH₃)₃ | H | H | S | 163–165 |
| —C₆H₅ | H | H | S | 190–192 |
| 3-CF₃—C₆H₄ | H | H | S | 158–160 |
| —CH(CH₃)₂ | H | CN | S | 195–197 |
| —C(CH₃)₃ | H | Cl | S | 176–179 |
| 3-CF₃—C₆H₄ | H | Cl | S | 186–188 |
| —C₆H₅ | H | Cl | S | 208–210 |
| —CH(CH₃)₂ | H | Cl | S | 219–221 |
| —C(CH₃)₃ | Cl | H | S | 216–218 |
| 3-CF₃—C₆H₄ | Cl | Cl | S | 242–244 |
| Cyclopropyl | Br | H | S | 236–238 |
| C₆H₅ | Br | H | S | 160–162 |
| C(CH₃)₃ | Cl | Cl | S | 137–139 |
| Cyclopropyl | Cl | Cl | S | 193–195 |
| C₆H₅ | Cl | Cl | S | 246–248 |
| Cyclopropyl | H | H | S | 188–190 |
| Cyclopropyl | H | Cl | S | 139–142 |
| C(CH₃)₃ | Br | H | S | 163–165 |
| C₆H₅ | H | H | O | 223–225 |
| 4-Cl—C₆H₄ | H | H | O | 247–249 |
| 2-F—C₆H₄ | H | H | O | 220–221 |
| C₆H₁₁ | H | H | O | 200–201 |
| C(CH₃)₃ | H | H | O | 178–180 |

TABLE b-continued

| R¹ | R² | R³ | X | mp. (°C.) |
|---|---|---|---|---|
| C(CH₃)₂CN | H | H | O | 188–190 |

TABLE c

Structure IV: HOOC and CONHR¹ on one side, R² and R³ on the other side of ring containing X

| R¹ | R² | R³ | X | mp. (°C.) |
|---|---|---|---|---|
| —C₆H₅ | H | H | S | 205–208 |
| —CH(CH₃)₂ | H | H | S | 161–169 |
| —C(CH₃)₃ | H | H | S | 127–139 |
| 3-Cl—C₆H₄ | H | H | S | 235–237 |
| 2-Cl—C₆H₄ | H | H | S | 186–187 |
| 3,4-Cl,Cl—C₆H₃ | H | H | S | 245–252 |
| 3-OCH₃—C₆H₄ | H | H | S | 170–173 |
| 4-Cl—C₆H₄ | H | H | S | 204–208 |
| 4-OCH₃—C₆H₄ | H | H | S | 250–253 |
| 3-CH₃—C₆H₄ | H | H | S | 220–223 |
| 3-F—C₆H₄ | H | H | S | 200–204 |
| 2,5-Dibrom-3-thienyl | H | H | S | |

TABLE c-continued

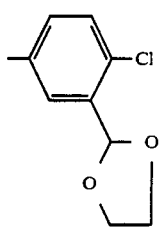

| R[1] | R[2] | R[3] | X | mp. (°C.) |
|---|---|---|---|---|
| 3-CF$_3$—C$_6$H$_4$ | H | H | S | 158-160 |
| —CH$_2$—C$_6$H$_5$ | H | H | S | 215-218 |
| 4-F—C$_6$H$_4$ | H | H | S | 218-220 |
| Cyclopropyl | H | H | S | 170-173 |
| —CH$_2$-Cyclopropyl | H | H | S | 165-168 |
| 2-F,4-Cl,5-OCH$_3$—C$_6$H$_2$ | H | H | S | 183-185 |
| (structure with Cl and dioxolane) | H | H | S | 206-208 |
| 2,5-Dichlor-3-thienyl | H | H | S | |
| —CH(CH$_3$)$_2$ | H | H | O | 171-174 |
| —C(CH$_3$)$_3$ | H | H | O | 190-194 |
| —C$_6$H$_5$ | H | H | O | 265-270 |
| 3-CF$_3$—C$_6$H$_4$ | H | H | O | 245-249 |
| 4-Cl—C$_6$H$_4$ | H | H | O | 251-255 |
| 3-CF$_3$—C$_6$H$_4$ | Cl | Cl | S | 148-150 |
| 3-CF$_3$—C$_6$H$_4$ | CH$_3$ | CH$_3$ | O | 140-141 |

Preparation of the end products Ia and Ib

EXAMPLE 6

N-Isopropylthiophene-3,4-carboximide

4-Isopropylaminocarbonylthiophene-3-carboxylic acid (3 g, 0.014 mol) and thionyl chloride (4.6 g, 0.064 mol) in 1,2-dichloroethane are refluxed for 5 hours. The mixture is then evaporated to dryness and the residue is chromatographed. Yield: 2.4 g, 88%; mp. 127°-129° C.

EXAMPLE 7

N-Phenyl-5-chlorothiophene-2,3-carboximide

5-Chloro-2-phenylaminocarbonylthiophene-3-carboxylic acid (1.1 g, 0.0039 mol) and thionyl chloride (4 ml, 0.055 mol) in 1,2-dichloroethane are refluxed for 5 hours. The mixture is then evaporated to dryness and the residue is chromatographed. Yield: 0.5 g, 49%; mp. 176°-178° C.

EXAMPLE 8

N-tert-Butyl-5-methylfuran-2,3-carboximide 2-tert-Butylaminocarbonyl-5-methylfuran-3-carboxylic acid (6.4 g, 0.028 mol) and p-toluenesulfonic acid (6.5 g, 0.034 mol) in pyridine are stirred for 12 hours at room temperature. The mixture is then evaporated to dryness and the residue is chromatographed. Yield: 4.9 g, 98%; mp. 131°-133° C.

Active Ingredient Table 1: Dicarboximides of the formula Ib

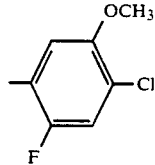

| Nr. | R[1] | R[2] | R[3] | X | mp. (°C.) |
|---|---|---|---|---|---|
| 1.001 | CH(CH$_3$)$_2$ | H | H | S | 127-129 |
| 1.002 | Cyclopropyl | H | H | S | 217-219 |
| 1.003 | C$_6$H$_5$ | H | H | S | 258-267 |
| 1.004 | 4-Cl—C$_6$H$_4$ | H | H | S | 212-215 |
| 1.005 | 3-CF$_3$—C$_6$H$_4$ | H | H | S | 110-112 |
| 1.006 | 3-Cl—C$_6$H$_4$ | H | H | S | 204-206 |
| 1.007 | (2-OCH$_3$,4-F,5-Cl-phenyl) | H | H | S | 183-185 |
| 1.008 | 2-F—C$_6$H$_4$ | H | H | S | 176-179 |
| 1.009 | C(CH$_3$)$_2$CN | H | H | S | 130-133 |
| 1.010 | Cyclopropyl | H | H | O | 174-176 |
| 1.011 | 3-CF$_3$—C$_6$H$_4$ | H | H | O | 61-63 |
| 1.012 | 4-Cl—C$_6$H$_4$ | H | H | O | 226-228 |
| 1.013 | C(CH$_3$)$_2$CN | H | H | O | 134-135 |
| 1.014 | 3-CF$_3$—C$_6$H$_4$ | CH$_3$ | CH$_3$ | O | 134-136 |
| 1.015 | 3-CF$_3$—C$_6$H$_4$ | CH$_2$CH$_2$CH$_3$ | CH$_2$CH$_2$CH$_3$ | O | 142-143 |
| 1.016 | Cyclopropyl | CH$_2$CH$_2$CH$_3$ | CH$_2$CH$_2$CH$_3$ | O | |

Active Ingredient Table 2: Dicarboximides of the formula Ia

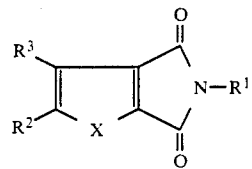

Ia

| Nr. | R¹ | R² | R³ | X | mp. (°C.) ¹H-NMR (DMSO-d₆, δ in ppm) |
|---|---|---|---|---|---|
| 2.001 | —C₆H₅ | H | H | S | 180-182 |
| 2.002 | 4-Cl—C₆H₄ | H | H | S | 206-211 |
| 2.003 | 3-CF₃—C₆H₄ | H | H | S | 113-115 |
| 2.004 | CH(CH₃)₂ | H | H | S | 96-98 |
| 2.005 | C(CH₃)₃ | H | H | S | 65-67 |
| 2.006 | C₆H₅ | Cl | H | S | 176-178 |
| 2.007 | Cyclopropyl | Cl | H | S | 109-111 |
| 2.008 | —CH(CH₃)₂ | Cl | H | S | 102-104 |
| 2.009 | —C(CH₃)₃ | Cl | H | S | 56-58 |
| 2.010 | —CH(CH₃)₂ | H | CN | S | 101-103 |
| 2.011 | —C₆H₅ | H | Cl | S | 154-156 |
| 2.012 | 2-Cl-5-(propenyl-CO₂CH₃ substituted)phenyl | H | H | S | 175-178 |
| 2.013 | 4-F-2-Cl-5-(OCH₂C≡CH)phenyl | H | H | S | 211-213 |
| 2.014 | 4-F-2-Cl-5-(OCH₂CO₂CH₃)phenyl | H | H | S | 135-140 |
| 2.015 | —CH(CH₃)₂ | CH₃ | H | O | 81-83 |
| 2.016 | —C₆H₅ | CH₃ | H | O | 165-167 |
| 2.017 | 4-Cl—C₆H₄ | CH₃ | H | O | 190-192 |
| 2.018 | —C(CH₃)₃ | CH₃ | H | O | 131-133 |
| 2.019 | 3-CF₃—C₆H₄ | CH₃ | H | O | 95-97 |
| 2.020 | 4-Cl—C₆H₄ | H | H | O | 191-193 |
| 2.021 | —C₆H₅ | H | H | O | 130-132 |
| 2.022 | —C(CH₃)₃ | H | H | O | 53-54 |
| 2.023 | Cyclopropyl | H | H | S | 149-151 |
| 2.024 | 3-CF₃—C₆H₄ | Cl | H | S | 149-151 |
| 2.025 | 2-F—C₆H₄ | Cl | H | S | 152-154 |
| 2.026 | 4-Cl—C₆H₄ | Cl | H | S | 131-133 |
| 2.027 | C₆H₁₁ | Cl | H | S | 147-149 |
| 2.028 | 1-Cyclopropyl-ethyl | Cl | H | S | 0.2-0.7(m, 4H); 1.55(d, 3H); 3.35(m, 1H); 7.15(s, 1H) |
| 2.029 | C(CH₃)₂CN | Cl | H | S | 63-65 |
| 2.030 | C₆H₅ | Br | H | S |  |
| 2.031 | C(CH₃)₃ | Br | H | S | 1.65(s, 9H); 7.20(s, 1H) |
| 2.032 | Cyclopropyl | Br | H | S | 101-102 |
| 2.033 | 3-CF₃—C₆H₄ | H | Cl | S | 172-174 |
| 2.034 | Cyclopropyl | H | Cl | S | 120-121 |
| 2.035 | Cyclopropyl | Cl | Cl | S | 95-97 |
| 2.036 | C(CH₃)₃ | Cl | Cl | S | 124-126 |
| 2.037 | C₆H₅ | Cl | Cl | S | 163-165 |
| 2.038 | 3-CF₃—C₆H₄ | Cl | Cl | S | 135-137 |
| 2.039 | C₆H₅ | OCH₃ | H | S | 123-125 |
| 2.040 | 3-CF₃—C₆H₄ | OCH₃ | H | S | 135-137 |

Active Ingredient Table 2: Dicarboximides of the formula Ia

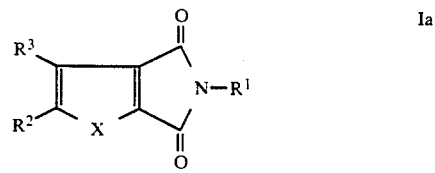

| Nr. | R¹ | R² | R³ | X | mp. (°C.) $^1$H-NMR (DMSO-$d_6$, δ in ppm) |
|---|---|---|---|---|---|
| 2.041 | Cyclopropyl | OCH₃ | H | S | 92–94 |
| 2.042 | 4-Cl—C₆H₄ | OCH₃ | H | S | 177–179 |
| 2.043 | C₆H₁₁ | CH₃ | H | S | 160–162 |
| 2.044 | Cyclopropyl | CH₃ | H | S | 114–116 |
| 2.045 | C₆H₅ | CH₃ | H | S | 154–156 |
| 2.046 | 3-CF₃—C₆H₄ | CH₃ | H | S | 122–124 |
| 2.047 | C(CH₃)₃ | CH₃ | H | S | 142–144 |
| 2.048 | 4-Cl—C₆H₄ | CH₃ | H | S | 220–222 |
| 2.049 | Cyclopropyl | C≡C—C₆H₅ | H | S | 157–159 |
| 2.050 | C₆H₅ | C₂H₅ | H | S | 120–122 |
| 2.051 | C₆H₅ | C≡C—C₆H₅ | H | S | 196–198 |
| 2.052 | Cyclopropyl | 2-Pyridyl | H | S | 190–193 |
| 2.053 | CH(CH₃)₂ | H | H | O | 65–67 |
| 2.054 | Cyclopropyl | H | H | O | 99–101 |
| 2.055 | Dimethylpropargyl | Cl | H | S | 65–68 |

Use Examples

The herbicidal action of the dicarboximides of the formula I can be demonstrated by greenhouse experiments:

The culture vessels used were plastic flowerpots containing loamy sand with about 3.0% of humus as a substrate. The seeds of the test plants were sown separately according to species.

In the preemergence treatment, the active ingredients, suspended or emulsified with water, were applied directly after sowing, by means of finely distributing nozzles. The vessels were lightly watered in order to promote germination and growth and were then covered with transparent plastic covers until the plants had started to grow. This covering ensured uniform germination of the test plants, unless they were adversely affected by the active ingredients.

For the postemergence treatment, the test plants were treated with the active ingredients, suspended or emulsified in water, at a height of growth of from 3 to 15 cm, depending on the form of growth. The application rate for the postemergence treatment was 1 kg/ha of active substance.

The plants were kept at 10°–25° C. or 20°–35° C., depending on species. The test period extended over from 2 to 4 weeks. During this time, the plants were tended and their reaction to the individual treatments was evaluated.

The evaluation was based on a scale from 0 to 100. 100 means no further growth of the plants or complete destruction of at least the above-ground parts and 0 means no damage, or normal growth.

The plants used in the greenhouse experiments consisted of the following species:

| Botanical name | Common name |
|---|---|
| Abutilon theophrasti | velvetleaf |
| Amaranthus retroflexus | redroot pigweed |
| Chenopodium album | common lambsquarters |
| Chrysanthemum | chrysanthemum |
| Solanum nigrum | black nightshade |

When 1 kg/ha of active substance is used in the postemergence method, undesirable broad-leaved plants can be very readily controlled with Example compounds Nos. 1.005 and 2.007, the active ingredients also being well tolerated by corn.

We claim:

1. A dicarboximide of the formula Ia

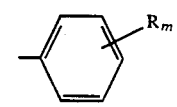

where

X is sulfur;

R¹ is C₃–C₈-cycloalkyl which may carry from one to three of the following radicals: halogen, C₁–C₄-alkyl, C₁–C₄-haloalkyl, C₁–C₄-alkoxy or C₁–C₄-haloalkyoxy;

C₁–C₆-alkyl which may carry from one to three of the following radicals: hydroxyl, halogen, cyano, C₃–C₈-cycloalkyl, C₁–C₄-alkoxy, C₁–C₄-haloalkoxy, C₁–C₄-alkythio, C₁–C₄-haloalkylthio, C₁–C₄-alkylamino, di-C₁–C₄-alkylamino or C₃–C₆-cycloalkylamino or a radical of the formula $$\underset{\phantom{X}}{\bigcirc}\!\!-\!R_m$$

in which R is cyano, nitro, halogen, C₁–C₄-alkyl, C₁–C₄-haloalkyl, C₁–C₄-alkoxy, C₁–C₄-haloalkoxy, C₂–C₄-alkynyloxy, C₁–C₄-alkylthio, C₁–C₄- haloalkythio, $C_3$-$C_6$-alkoxycarbonylalkoxy, $C_1$-$C_4$-alkoxycarbonyl, 2-alkoxycarbonylprop-1-enyl, $C_1$-$C_4$-alkanoyl, $C_1$-$C_4$-haloalkanoyl, formyl, dioxolanyl or phenyl, m is 0, 1, 2 or 3, and the radicals R may be different when m is 2 or 3;

$C_1$-$C_4$-alkoxy, $C_2$-$C_6$-cyanoalkyl, $C_3$-$C_6$-alkenyl, $C_3$-$C_6$-alkynyl, phenyl or naphthyl, where these groups may carry from one to three of the radicals stated for R;

one of $R^2$ and $R^3$ is chlorine, bromine, methyl, or cyano;

the remaining one of $R^2$ and $R^3$ is hydrogen or chlorine; and agriculturally useable salts thereof.

2. A dicarboximide of the formula Ia;

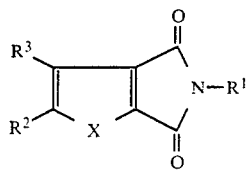

where

X is sulfur;

$R^1$ is $C_3$-$C_8$-cycloalkyl which may carry from one to three of the following radicals: halogen, $C_1$-$C_4$-alkyl, $C_1$-$C_4$-haloalkyl, $C_1$-$C_4$-alkoxy or $C_1$-$C_4$-haloalkyoxy;

$C_1$-$C_6$-alkyl which may carry from one to three of the following radicals: hydroxyl, halogen, cyano, $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di-$C_1$-$C_4$-alkylamino or $C_3$-$C_6$-cycloalkylamino or a radical of the formula

in which R is cyano, nitro, halogen, $C_1$-$C_4$-alkyl, $C_1$-$C_4$-haloalkyl, $C_1$-$C_4$-alkoxy, $C_1$-$C_4$-haloalkoxy, $C_2$-$C_4$-alkynyloxy, $C_1$-$C_4$-alkylthio, $C_1$-$C_4$-haloalkylthio, $C_3$-$C_6$-alkoxycarbonylalkoxy, $C_1$-$C_4$-alkoxycarbonyl, 2-alkoxycarbonylprop-1-enyl, $C_1$-$C_4$-alkanoyl, $C_1$-$C_4$-haloalkanoyl, formyl, dioxolanyl or phenyl, m is 0, 1, 2 or 3, and the radicals R may be different when m is 2 or 3;

$C_1$-$C_4$-alkoxy, $C_2$-$C_6$-cyanoalkyl, $C_3$-$C_6$-alkenyl, $C_3$-$C_6$-alkynyl or naphthyl, where these groups may carry from one to three of the radicals stated for R;

phenyl which carries from one to three of the radicals stated for R;

one of $R^2$ and $R^3$ is hydrogen;

the remaining one of $R^2$ and $R^3$ is chlorine, bromine, methyl, or cyano;

and agriculturally useable salts thereof.

3. A dicarboximide of the formula Ia;

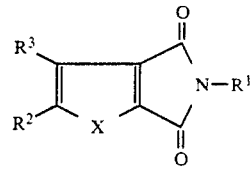

where

X is oxygen;

$R^1$ is $C_3$-$C_8$-cycloalkyl which may carry from one to three of the following radicals: halogen, $C_1$-$C_4$-alkyl, $C_1$-$C_4$-haloalkyl, $C_1$-$C_4$-alkoxy or $C_1$-$C_4$-haloalkoxy;

$C_1$-$C_6$-alkyl which may carry from one to three of the following radicals: hydroxyl, halogen, cyano, $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di-$C_1$-$C_4$-alkylamino or $C_3$-$C_6$-cycloalkylamino or a radical of the formula

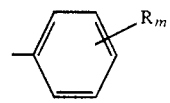

in which R is cyano, nitro, halogen, $C_1$-$C_4$-alkyl, $C_1$-$C_4$-haloalkyl, $C_1$-$C_4$-alkoxy, $C_1$-$C_4$-haloalkoxy, $C_2$-$C_4$-alkynyloxy, $C_1$-$C_4$-alkylthio, $C_1$-$C_4$-haloalkylthio, $C_3$-$C_6$-alkoxycarbonylalkoxy, $C_1$-$C_4$-alkoxycarbonyl, 2-alkoxycarbonylprop-1-enyl, $C_1$-$C_4$-alkanoyl, $C_1$-$C_4$-haloalkanoyl, formyl, dioxolanyl or phenyl, m is 0, 1, 2 or 3, and the radicals R may be different when m is 2 or 3;

$C_1$-$C_4$-alkoxy, $C_2$-$C_6$-cyanoalkyl, $C_3$-$C_6$-alkenyl, $C_3$-$C_6$-alkynyl, phenyl or naphthyl, where these groups may carry from one to three of the radicals stated for R;

$R_2$ and $R_3$ are each independently hydrogen, chlorine, bromine, methyl, or cyano;

and agriculturally useable salts thereof.

4. A dicarboximide of the formula Ia

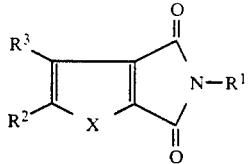

where

X is sulfur;

$R^1$ is $C_3$-$C_8$-cycloalkyl which may carry from one to three of the following radicals: halogen, $C_1$-$C_4$-alkyl, $C_1$-$C_4$-haloalkyl, $C_1$-$C_4$-alkoxy or $C_1$-$C_4$-haloalkoxy;

$C_1$-$C_6$-alkyl which may carry from one to three of the following radicals: hydroxyl, halogen, cyano, $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di-$C_1$-$C_4$-alkylamino, $C_3$-$C_6$-cycloalkylamino or a radical of the formula

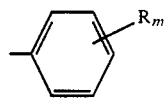

in which R is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$–$C_6$-alkoxycarbonylalkoxy, $C_1$–$C_4$-alkoxycarbonyl, 2-alkoxycarbonyl-prop-1-enyl, $C_1$–$C_4$-alkanoyl, $C_1$–$C_4$-haloalkanoyl, formyl, dioxolanyl or phenyl, m is 0, 1, 2 or 3, and the radicals R may be different when m is 2 or 3;

$C_1$–$C_4$-alkoxy, $C_2$–$C_6$-cyanoalkyl, $C_3$–$C_6$-alkenyl, $C_3$–$C_6$-alkynyl, phenyl or naphthyl, where these groups may carry from one to three of the radicals stated for R;

$R^2$ and $R^3$ are each independently nitro; cyano; halogen;

amino which may carry one or two $C_1$–$C_4$-alkyl groups or a $C_1$–$C_4$-alkylcarbonyl group;

$C_1$–$C_4$-alkoxy or $C_1$–$C_4$-alkylthio, where these groups may carry from one to nine halogen atoms;

$C_1$–$C_4$-alkylsulfonyl; $C_1$–$C_4$-haloalkylsulfonyl;

$C_2$–$C_6$-alkenyl, $C_2$–$C_6$-alkynyl, phenyl, phenoxy or phenylthio, where these groups may carry from one to three of the radicals stated for R;

hydroxyl;

$C_3$–$C_8$-cycloalkyl which may carry from one to three of the following radicals: halogen, $C_1$–$C_4$-alkyl, $C_1$–$C_4$-haloalkyl, $C_1$–$C_4$-alkoxy or $C_1$–$C_4$-haloalkoxy;

$C_1$–$C_6$-alkyl which may carry from one to three of the following radicals: hydroxyl, halogen, cyano, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_3$–$C_6$-cycloalkylamino or a radical of the formula

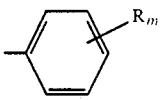

in which R is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$–$C_6$-alkoxycarbonylalkoxy, $C_1$–$C_4$-alkoxycarbonyl, 2-alkoxycarbonylprop-1-enyl, $C_1$–$C_4$-alkanoyl, $C_1$–$C_4$-haloalkanoyl, formyl, dioxolanyl or phenyl, m is 0, 1, 2 or 3, and the radicals R may be different when m is 2 or 3;

$C_2$–$C_6$-cyanoalkyl or naphthyl, where these groups may carry from one to three of the radicals stated for R;

$C_1$–$C_4$-alkoxy which may carry from one to three cyano, nitro, $C_1$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$–$C_6$-alkoxycarbonylalkoxy, $C_1$–$C_4$-alkoxycarbonyl, 2-alkoxycarbonylprop-1-enyl, $C_1$–$C_4$-alkanoyl, $C_1$–$C_4$-haloalkanoyl, formyl, dioxolanyl or phenyl, and agriculturally useable salts thereof.

5. A dicarboximide of the formula Ia

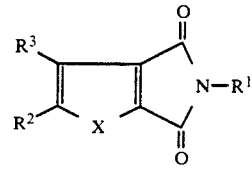

where
X is sulfur;
$R^1$ is
  $C_3$–$C_8$-cycloalkyl which may carry from one to three of the following radicals: halogen, $C_1$–$C_4$-alkyl, $C_1$–$C_4$-haloalkyl, $C_1$–$C_4$-alkoxy or $C_1$–$C_4$-haloalkoxy;
  $C_1$–$C_6$-alkyl which may carry from one to three of the following radicals: hydroxyl, halogen, cyano, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_3$–$C_6$-cycloalkylamino or a radical of the formula

in which R is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$–$C_6$-alkoxycarbonylalkoxy, $C_1$–$C_4$-alkoxycarbonyl, 2-alkoxycarbonylprop-1-enyl, $C_1$–$C_4$-alkanoyl, $C_1$–$C_4$-haloalkanoyl, formyl, dioxolanyl or phenyl, m is 0, 1, 2 or 3, and the radicals R may be different when m is 2 or 3;

$C_1$–$C_4$-alkoxy, $C_2$–$C_6$-cyanoalkyl, $C_3$–$C_6$-alkenyl, $C_3$–$C_6$-alkynyl or naphthyl, where these groups may carry from one to three of the radicals stated for R;

phenyl which may carry from one to three of the following radicals: cyano, halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$–$C_6$-alkoxycarbonylalkoxy, $C_1$–$C_4$-alkoxycarbonyl, 2-alkoxycarbonyl-prop-1-enyl, $C_1$–$C_4$-alkanoyl, $C_1$–$C_4$-haloalkanoyl, formyl, dioxolanyl or phenyl;

phenyl which carried one nitro radical and which may carry one or two of the following radicals: cyano, halogen, $C_2$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$–$C_6$-alkoxycarbonylalkoxy, $C_1$–$C_4$-alkoxycarbonyl, 2-alkoxycarbonyl-prop-1-enyl, $C_1$–$C_4$-alkanoyl, $C_1$–$C_4$-haloalkanoyl, formyl, dioxolanyl or phenyl;

phenyl which carried one nitro radical, one $C_1$-alkyl radical and one of the following radicals: cyano, halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkynyloxy, $C_1$–$C_4$-alkylthio, $C_1$–$C_4$-haloalkylthio, $C_3$-$C_6$-alkoxycarbonylalkoxy, $C_1$-$C_4$-alkoxycarbonyl, 2-alkoxycarbonyl-prop-1-enyl, $C_1$-$C_4$-alkanoyl, $C_1$-$C_4$-haloalkanoyl, formyl, dioxolanyl or phenyl;

phenyl which carries two nitros and which may carry one of the following radicals: cyano, halogen, $C_1$-$C_4$-alkyl, $C_1$-$C_4$-haloalkyl, $C_1$-$C_4$-alkoxy, $C_1$-$C_4$-haloalkoxy, $C_2$-$C_4$-alkynyloxy, $C_1$-$C_4$-alkylthio, $C_1$-$C_4$-haloalkylthio, $C_3$-$C_6$-alkoxycarbonylalkoxy, $C_1$-$C_4$-alkoxycarbonyl, 2-alkoxycarbonylprop-1-enyl, $C_1$-$C_4$-alkanoyl, $C_1$-$C_4$-haloalkanoyl, formyl, dioxolanyl or phenyl; or trinitrophenyl;

one of $R^2$ and $R^3$ is hydrogen; and the remaining one of $R^2$ and $R^3$ is nitro; cyano; halogen;

amino which may carry one or two $C_1$-$C_4$-alkyl groups or a $C_1$-$C_4$-alkylcarbonyl group;

$C_1$-$C_4$-alkoxy or $C_1$-$C_4$-alkylthio, where these groups may carry from one to nine halogen atoms;

$C_1$-$C_4$-alkylsulfonyl; $C_1$-$C_4$-haloalkylsulfonyl; or $C_2$-$C_6$-alkenyl, $C_2$-$C_6$-alkynyl, phenyl, phenoxy or phenylthio, where these groups may carry from one to three of the radicals stated for R;

one of the groups stated for $R^1$; or phenyl which carries a nitro radical and a $C_1$-alkyl radical;

and agriculturally useable salts thereof.

6. The dicarboximide of claim 4, where $R^1$ is cyclopropyl, $R^2$ is chloro and $R^3$ is hydrogen, and agriculturally useable salts thereof.

7. A herbicidal composition which comprises inert additives and an effective amount of a dicarboximide of the formula Ia as described in claim 4.

8. A method for controlling undesirable plant growth, wherein the undesired plants or their habitat are or is treated with a herbicidal amount of a dicarboximide Ia as described in claim 4.

* * * * *